(12) United States Patent
Bisogni et al.

(10) Patent No.: US 7,589,185 B2
(45) Date of Patent: Sep. 15, 2009

(54) NUCLEOTIDE SEQUENCES AND PROTEIN(S) ENCODED BY SUCH NUCLEOTIDES FOR MODULATION OF APOPTOSIS

(75) Inventors: Rita Bisogni, Naples (IT); Annalisa Lamberti, Naples (IT); Antonello Petrella, Naples (IT); Maria Fiammetta Romano, Naples (IT); Maria Caterina Turco, Avellino (IT); Salvatore Venuta, Naples (IT)

(73) Assignee: Universita' degli Studi di Catanzaro "Magna Graecia", Catanzaro (IT)

( * ) Notice: Subject to any disclaimer, the term of this patent is extended or adjusted under 35 U.S.C. 154(b) by 101 days.

(21) Appl. No.: 10/250,987

(22) PCT Filed: Jan. 10, 2002

(86) PCT No.: PCT/EP02/00171

§ 371 (c)(1),
(2), (4) Date: Nov. 25, 2003

(87) PCT Pub. No.: WO02/055553

PCT Pub. Date: Jul. 18, 2002

(65) Prior Publication Data

US 2004/0072163 A1 Apr. 15, 2004

(30) Foreign Application Priority Data

Jan. 10, 2001 (IT) .................. RM2001A0005

(51) Int. Cl.
*C07H 21/02* (2006.01)
(52) U.S. Cl. ..................................... 536/23.1
(58) Field of Classification Search ................. 536/23.1
See application file for complete search history.

(56) References Cited

U.S. PATENT DOCUMENTS

| | | | | |
|---|---|---|---|---|
| 5,908,973 | A * | 6/1999 | Abu-Bakar et al. | ......... 800/295 |
| 6,617,156 | B1 * | 9/2003 | Doucette-Stamm et al. | ...... 435/320.1 |
| 6,812,339 | B1 * | 11/2004 | Venter et al. | ............. 536/24.31 |
| 2005/0266560 | A1 * | 12/2005 | Preuss et al. | ................. 435/419 |

OTHER PUBLICATIONS

Garnier, Genbank submission, U74659, Dec. 1996.*
Granziero et al, Adoptive immunotherapy prevents prostate cancer in a transgenic animal model. Eur. J, Immunol 1999. vol. 29, pp. 1127-1138.*
Byers, What can randomized controlled trials tell us about nutrition and cancer prevention. CA Cancer J Clin. Nov./Dec. 1999, vol. 49, No. 6, pp. 353-361.*
Freshney (Culture of Animal Cells, A Manual of Basic Technique, Alan R. Liss, Inc., 1983, New York, p. 4).*
1997/1998 Stratagene catalog (p. 118, 1997/1998).*
Freshney (Culture of Animal Cells, A Manual of Basic Technique, Alan R. Liss, Inc., 1983, New York, p. 4).*
Rolland (Advanced Drug Delivery Reviews, 2005, 57:669-673).*
Garnier et al (GenBank submission U74659, Dec. 3, 1996).*
Two sequence comparisons.*
Garnier et al (The Journal of Neuroscience, Jun. 1997, 17(12):4591-4599).*
Granelli-Pipemo et al., "Nuclear Transcription Factors that Bind to Elements of the IL-2 Promoter," J. Immunology 147:2734-2739, 1991.
Green, "Apoptotic Pathways: Paper Wraps Stone Blunts Scissors," Cell 102:1-4, 2000.
Lamberti et al., "Regulation of Cell Survival in CD95-induced T Cell Apoptosis: Role of NF-kB/Rel Transcription Factors," Apoptosis 4:179-186, 1999.
Liang et al., "Differential Display : A General Protocol," Methods in Molecular Biology, vol .85, ed. P. Liang and A.B. Pardee, Humana Press Inc., Totowa, New Jersey.
Nicoletti et al., "A Rapid and Simple Method for Measuring Thymocyte Apoptosis by Propidium Iodide Staining and Flow Cytometry," J. Immunological Methods 139:271-279, 1991.
Romano et al., "Amifostine Inhibits Hematopoietic Progenitor Cell Apoptosis by Activating NF-kB/Rel Transcription Factors," Blood 94:4060-4066, 1999.
Romano et al., "Enhancement of Cytosine Arabinoside-induced Apoptosis in Human Myeloblastic Leukemia Cells by NF-kB/Rel-specific Decoy Oligodeoxynucleotides," Gene Therapy 7:1234-1237, 2000.
Romano et al., "Triggering of CD40 Antigen Inhibits Fludarabine-Induced Apoptosis in B Chronic Lymphocytic Leukemia Cells," Blood 92:990-995, 1998.
Tassone et al., "CD36 is Rapidly and Transiently Upregulated on Phytohemagglutinin (PHA)-stimulated Peripheral Blood·Lymphocytes. Analysis by a New Monoclonal Antibody (UN7)," Tissue Antigens 51:671-675 (1998).
Granelli-Piperno et al., "Nuclear Transcription Factors that Bind to Elements of the IL-2 Promoter," J. Immunology 147:2734-2739, 1991.
Green, "Apoptotic Pathways: Paper Wraps Stone Blunts Scissors," Cell 102:1-4, 2000.
Lamberti et al., "Regulation of Cell Survival in CD95-induced T Cell Apoptosis: Role of NF-kB/Rel Transcription Factors," Apoptosis 4:179-186, 1999.
Liang et al., "Differential Display : A General Protocol," Methods in Molecular Biology, vol .85, ed. P. Liang and A.B. Pardee, Humana Press Inc., Totowa, New Jersey, 1997.

(Continued)

*Primary Examiner*—Sean E Aeder
(74) *Attorney, Agent, or Firm*—Clark & Elbing LLP

(57) ABSTRACT

It is described a nucleotide sequence and a corresponding protein for which a role and utility in the regulation of programmed cell death or apoptosis are defined. Applications and uses of the sequence and corresponding protein concern all the physiologic and pathologic processes that involve cell death (neoplasias, degenerative diseases, tissue infarcts, autoimmune diseases, differentiation processes, etc.).

12 Claims, 32 Drawing Sheets

OTHER PUBLICATIONS

Nicoletti et al., "A Rapid and Simple Method for Measuring Thymocyte Apoptosis by Propidium Iodide Staining and Flow Cytometry," J. Immunological Methods 139:271-279, 1991.

Romano et al., "Amifostine Inhibits Hematopoietic Progenitor Cell Apoptosis by Activating NF-kB/Rel Transcription Factors," Blood 94:4060-4066, 1999.

Romano et al., "Enhancement of Cytosine Arabinoside-induced Apoptosis in Human Myeloblastic Leukemia Cells by NF-kB/Rel-specific Decoy Oligodeoxynucleotides," Gene Therapy 7:1234-1237, 2000.

Romano et al., "Triggering of CD40 Antigen Inhibits Fludarabine-Induced Apoptosis in B Chronic Lymphocytic Leukemia Cells," Blood 92:990-995, 1998.

Tassone et al., "CD36 is Rapidly and Transiently Upregulated on Phytohemagglutinin (PHA)-stimulated Peripheral Blood Lymphocytes. Analysis by a New Monoclonal Antibody (UN7)," Tissue Antigens 51:671-675 (1998).

'Modulation of Cell Apoptosis by AIR' Leukemia 2 pgs. 2007.

Turco et al., "Modulation of Cell Apoptosis by AIR," Leukemia 21(12):2557, 2007.

* cited by examiner

NUCLEOTIDE SEQUENCES AND PROTEIN(S) ENCODED BY SUCH NUCLEOTIDES FOR MODULATION OF APOPTOSIS

This application is a U.S. National Stage application of, and claims priority under 35 U.S.C. 371 from, International Application No. PCT/EP02/00171, filed on Jan. 10, 2002, which was published in English on Jul. 18, 2002, and claims priority from Italian Application No. RM01A000005, filed on Jan. 10, 2001.

FIELD OF THE INVENTION

The present invention concerns a nucleotide sequence and a corresponding protein able to regulate apoptosis.

More particularly the invention concerns the use of such sequence or such protein or their parts as apoptosis regulators.

The invention provides novel polynucleotides and proteins encoded by such polynucleotides, along with therapeutic, diagnostic and research utilities for these polynucleotides and proteins.

More generally the invention refers to the use of such polynucleotides and proteins or parts of them for research, diagnostic and therapeutic purposes in cell death—involving diseases, and for modulation of cell survival and/or death.

BACKGROUND

It is well known that our cells produce, from their DNA, messenger RNAs (mRNAs) and corresponding proteins, many of which are known while many are not yet known, and by which biologic activities are regulated. By studying such mRNAs and constructing corresponding cDNAs (complementary cDNAs), it is possible to find new molecules and new utilities to regulate cell biologic activities and modify their pathologic alterations.

Programmed cell death, or apoptosis (ref. 1), is a fundamental process in the regulation of many biologic processes. Indeed, either in differentiation processes and in mature tissues, balance between cellular compartments is determined by the ratio between cellular proliferation and programmed cell death. Alterations, either as a deregulated stimulation or a defective functioning, of apoptosis underlie many pathologies. Tissue degenerative diseases (of brain, such as in several forms of dementia, and of various other tissues) or diseases due to tissue acute damages (like infarcts of hearth, brain or other organs) or to excessive and/or deregulated inflammation involve apoptosis. Finding elements and tools that regulate apoptosis is important since it can allow, in these cases, to block the death process that causes the disease. On the other hand, in other pathologies, such as autoimmune diseases, apoptosis deregulation leads to aberrant expansion of cells, that attack our organism. Elements able to regulate apoptosis can, in these cases, equilibrate the death process in these cells and cure the disease. In other pathologies, including first of all neoplasias, cells display a reduced sensitivity to apoptosis and this leads to two consequences: one in pathogenesis, since the reduced sensitivity to apoptosis underlies the neoplastic clone expansion, and the other in therapy, since such reduced sensitivity determines neoplastic cell resistance to therapies (chemo- and radiotherapies, therapies with biological modifiers, etc.) that should induce their death. Finding elements that regulate apoptosis can therefore allow to either fight the arising of neoplasia and determine therapeutically neoplastic cell death. This indeed today represents a fundamental approach of research in oncology. Finally, in other conditions like ageing, or in hyperplastic or dysplastic alterations like myelodisplastic diseases and others, apoptosis exerts a fundamental role and to be able to affect it can allow to affect the process.

Several apoptosis-regulating elements are known: caspases, intracellular enzymes that can induce cell death, and their inhibitors or activators; proteins of mitochondrion, an organelle in which fundamental apoptosis-regulating processes take place; and other molecules. However, evidence in literature indicate that there are other elements, not yet characterised, that regulate apoptosis (1). For example, apoptosis can be regulated by the activity of transcription factors NF-κB/Rel (Ref. 6). However, it is still poorly known what are all genes on which these transcription factors act in regulating apoptosis. We therefore aimed at identifying, through modulating NF-κB/Rel activity, novel nucleotide sequences able to affect apoptosis.

SUMMARY OF THE INVENTION

A nucleotide sequence and a corresponding protein able to regulate apoptosis have been found and are object of the present invention. It has been found that also parts of them are able to exert a regulatory activity.

It is an object of the present invention an isolated nucleotide sequence (AIR), its parts, and corresponding protein(s) (Air and others) able to modulate cell survival and/or death.

Accordingly the present invention include: isolated AIR polynucleotide sequence, indicated as SEQ ID NO 1, including recombinant DNA molecules, cloned genes or degenerate variants thereof, especially naturally occurring variants such as allelic variants; AIR parts; particularly: AIR ORF 1, that corresponds to a possible variant of the sequence, and is indicated as SEQ ID NO 2; AIR ORF 2, indicated as SEQ ID NO 3; AIR ORF 3, indicated as SEQ ID NO 4; AIR ORF 4, indicated as SEQ ID NO 5. The compositions of the present invention also include: AIR-based antisense oligonucleotides, including, but not limited to, those indicated as SEQ ID NO 6, SEQ ID NO 7, SEQ ID NO 8; AIR-based nonsense oligonucleotides, indicated as SEQ ID NO 9, SEQ ID NO 10 and SEQ ID NO 11; polypeptide sequences encoded by AIR sequence or its parts, including, but not limited to: SEQ ID NO 12 (encoded by ORF 1); SEQ ID NO 13 (Air, encoded by ORF 2); SEQ ID NO 14 (encoded by ORF 3); SEQ ID NO 15 (encoded by ORF 4). The compositions of the present invention further include antibodies, including the polyclonal and monoclonal antibodies described in the present invention, that specifically recognize one or more epitopes present on such polypeptides.

The polynucleotides of the invention additionally include the complement of any of the polynucleotides recited above.

The isolated polypeptides of the invention include, but are not limited to, a polypeptide comprising the amino acid sequence of SEQ ID NO 12, SEQ ID NO 13, SEQ ID NO 14, SEQ ID NO 15 and the amino acid sequence of SEQ ID NO 16, SEQ ID NO 17, SEQ ID NO 18.

The polypeptides of the invention additionally include, but are not limited to, polypeptides resulting from those of SEQ ID NO 12, SEQ ID NO 13, SEQ ID NO 14, SEQ ID NO 15, SEQ ID NO 16, SEQ ID NO 17, SEQ ID NO 18 following their processing in an eukaryotic cell, and their precursor, partially and fully mature forms.

Another object are the compositions comprising such polynucleotide sequences and corresponding protein(s), and AIR-based reagents, for research, diagnostic and therapeutic purposes in cell death-involving diseases, and for modulation of cell survival and/or death.

The compositions of the present invention additionally include vectors, including expression vectors, containing the polynucleotide sequences of the invention or their parts; cells genetically engineered to contain such polynucleotide sequences or their parts and cells genetically engineered to express such polynucleotide sequences or their parts.

Protein compositions of the present invention may further comprise an acceptable carrier, such as pharmaceutically acceptable carrier.

The invention also relates to methods for producing a peptide or polypeptide comprising growing a culture of cells expressing the polynucleotide sequence of the invention or its parts in a suitable culture medium, and purifying the protein from the culture. Preferred embodiments include those in which the protein produced by such process is a mature form of the protein.

Another object of the present invention is the use of such nucleotide and aminoacidic sequences for research, diagnosis and for therapy to treat all pathologies that depend on or involve the apoptosis mechanism, particularly: tissue degenerative diseases (of brain, such as in several forms of dementia, and of various other tissues) or diseases due to tissue acute damages (like infarcts of hearth, brain or other organs) or to excessive and/or deregulated inflammation; autoimmune diseases, involving the aberrant expansion of cells, that attack our organism; neoplasias, since the reduced sensitivity to apoptosis underlies the neoplastic clone expansion, and determines neoplastic cell resistance to therapies (chemo- and radiotherapies, therapies with biological modifiers, etc.) that should induce their death; ageing, or in hyperplastic or dysplastic alterations like myelodisplastic diseases and others.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art, as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide.

Methods are also provided for preventing, treating or ameliorating a medical condition, which comprises administering to a mammalian subject a therapeutically effective amount of a composition comprising a protein of the present invention and a pharmaceutically acceptable carrier.

In particular, the polypeptides and polynucleotides of the invention, and AIR- or Air-based reagents, can be utilized, for example, as part of methods for diagnosis, staging or therapy in diseases such as: acute or chronic tissue damages, such as heart, kidney, brain or other organ ischaemia, HIV-related damage of brain or other tissues, skeletal muscle disorders; transplantation rejection; chronic degenerative disorders such as Parkinson's disease, amyotrophic lateral sclerosis and others, etc.; neoplastic, autoimmune and other diseases involving excessive or defective apoptosis; allergies; tissue repair or wound healing, treatment of surgical incisions, and ulcers, such as stomach or diabetic ulcers; etc. In addition, the polynucleotides and polypeptides of the invention can further be utilized, for example, as part of methods for the prevention and/or treatment of disorders recited above, and disorders involving excessive or defective cell survival and/or death.

The methods of the present invention further relate to methods for detecting the presence of the polynucleotides or polypeptides of the invention in a sample. Such methods can, for example, be utilized as part of prognostic and diagnostic evaluation of disorders as recited above and for the identification of subjects exhibiting a predisposition to such conditions. Furthermore, the invention provides methods for evaluating the efficacy of drugs, and monitoring the progress of patients, involved in clinical trials for the treatment of disorders as recited above.

The invention also provides methods for the identification of compounds that modulate the expression of the polynucleotides and/or polypeptides of the invention. Such methods can be utilized, for example, for the identification of compounds that can ameliorate symptoms of disorders as recited above. Such methods can include, but are not limited to, assays for identifying compounds and other substances that interact with (e.g., bind to) the polypeptides of the invention. The methods of the invention also include methods for the treatment of disorders as recited above which may involve the administration of such compounds to individuals exhibiting symptoms or tendencies related to disorders as recited above. In addition, the invention encompasses methods for treating diseases or disorders as recited above by administering compounds and other substances that modulate the overall activity of the target gene products. Compounds and other substances can effect such modulation either on the level of target gene expression or target protein activity.

Further objects of the invention will become evident from the following detailed description of the invention.

DEFINITIONS

In the description the following definitions were used.

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

The terms "oligonucleotides" or "nucleic acid probes" are prepared based on the polynucleotide sequences provided in the present invention. Oligonucleotides comprise portions of such a polynucleotide sequence having at least about 10 nucleotides and usually at least about 15 nucleotides. Nucleic acid probes comprise portions of such a polynucleotide sequence having fewer nucleotides than about 6 kb, usually less than about 1 kb. After appropriate testing to eliminate false positives, these probes may, for example, be used to determine whether specific mRNA molecules are present in a cell or tissue or to isolate similar nucleic acid sequences from chromosomal DNA, as known to those skilled in the art.

The term "probes" includes naturally occurring or recombinant or chemically synthesized single- or double-stranded nucleic acids. They may be labeled by nick translation, Klenow fill-in reaction, PCR or other methods well known in the art.

The term "stringent" is used to refer to conditions that are commonly understood in the art as stringent. Stringent conditions can include highly stringent conditions (i.e., hybridization to filter-bound DNA under in 0.5 M NaHPO4, 7% sodium dodecyl sulfate (SDS), 1 mM EDT A at 65° C., and washing in 0.1×SSC/0.1% SDS at 68° C.), and moderately stringent conditions (i.e., washing in 0.2×SSC/0.1% SDS at 42° C.).

In instances wherein hybridization of deoxyoligonucleotides is concerned, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term "recombinant", when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., E. Coli will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (a) a genetic element or elements having a regulatory role in gene expression, for example, promoters or enhancers, (b) a structural or coding sequence which is transcribed into mRNA and translated into protein, and (c) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term "recombinant expression system" means host cells, which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells, which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame", ORF, means a series of nucleotide triplets coding for amino acids without any termination codons and is a sequence translatable into protein.

The term "expression modulating fragment," EMF, means a series of nucleotides which modulates the expression of an operably linked ORF or another EMF.

The term "uptake modulating fragment," UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. A UMF will increase the frequency of uptake of a linked marker sequence.

The term "active" refers to those forms of the polypeptide which retain the biologic and/or immunologic activities of any naturally occurring polypeptide.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20%, i.e. the number of individual residue substitutions, additions, and/or deletions in a substantially equivalent sequence, as compared to the corresponding reference sequence, divided by the total number of residues in the substantially equivalent sequenc is about 0.2 or less). Such a sequence is said to have 80% sequence identity to the listed sequence. Compared to substantially equivalent, mutant, amino acid sequences according to the invention, substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation, which creates a spurious stop codon) should be disregarded.

Nucleic acid sequences encoding such substantially equivalent sequences, sequences of the recited percent identities can routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment", "portion" or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes, which produce various restriction sites, may be le introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like (but water, buffers, and other small molecules, especially molecules having a molecular weight of less than 1000 dalton, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same. The terms "isolated" and "purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

The term "secreted" protein includes a protein that is transported across or through a membrane, including transport as a result of signal sequences in its amino acid sequence when it is expressed in a suitable host cell. "Secreted" proteins also includes without limitation proteins secreted wholly (e.g., soluble proteins) or partially (e.g., receptors) from the cell in which they are expressed. "Secreted" proteins also include without limitation proteins, which are transported across the membrane of the endoplasmic reticulum. "Secreted" proteins are also intended to include proteins containing non-typical signal sequences. Each of the above terms is meant to encompass all that is described for each, unless the context dictates otherwise.

DETAILED DESCRIPTION OF THE INVENTION

Figure 1A:
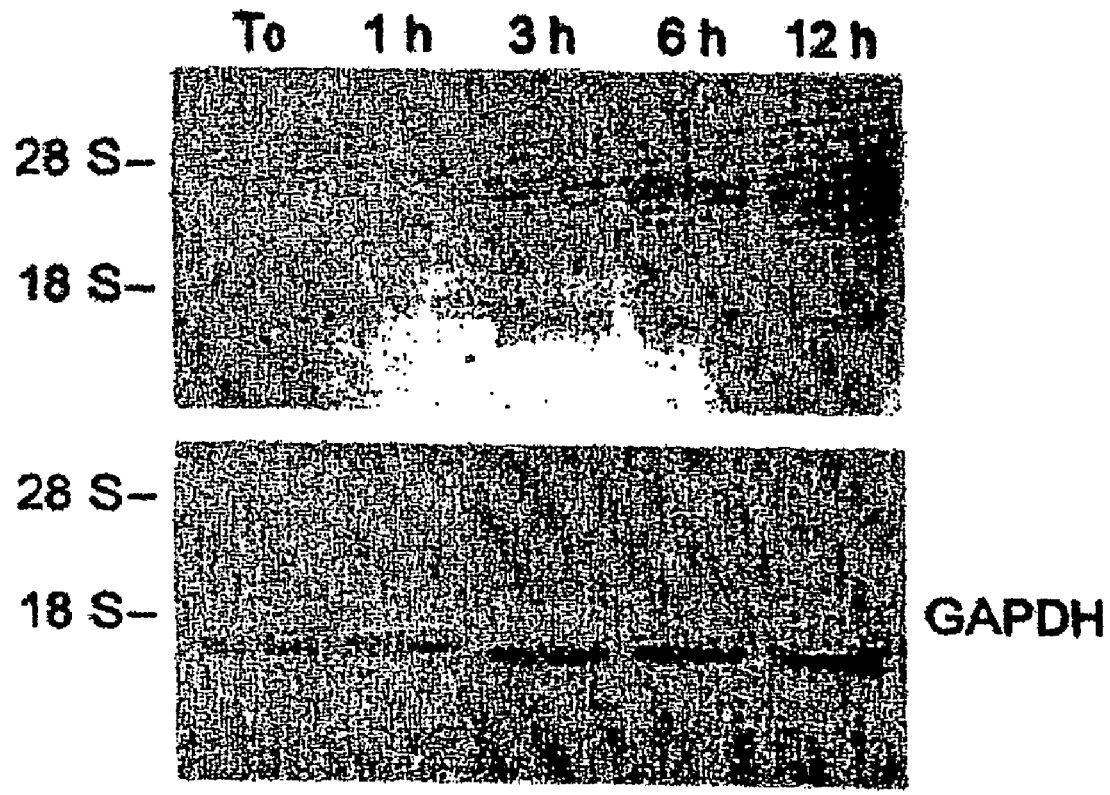
FIG. 1A—Expression of the sequence SEQ ID NO 1 in human cells. (A panel) Northern blot of mRNA from Jurkat cells unstimulated (T0) or stimulated with the anti-Fas monoclonal antibody (mAb) CH-11 for different time intervals. GAPDH gene expression is shown for comparative purposes.

Polynucleotides and Nucleic Acids of the Invention

Nucleotide and amino acid sequences of the invention are reported as SEQ ID NOS: 1-21. According to the present invention, the nucleotide sequences including the SEQ ID NO 1 or its parts, as cDNA or corresponding mRNA, and protein comprising the polypeptide indicated as SEQ ID NO 13, and partial aminoacidic sequences corresponding to the above recited nucleotide sequences, can be utilised to modulate cell death and/or proliferation and/or homeostasis of a cellular compartment, i.e. the number of cells in a tissue.

Fragments of the proteins of the present invention, which are capable of exhibiting biological activity, are also encompassed by the present invention. Fragments of the protein may be in linear form or they may be cyclized using known methods. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides both full-length and mature forms (e.g. without a signal sequence) of the disclosed proteins. The full-length form of the proteins is identified in the sequence listing by translation of the nucleotide sequence of each disclosed clone. The mature form of such protein may be obtained by expression of the disclosed full-length polynucleotide in a suitable mammalian cell or other host cell. The sequence of the mature form of the protein is also determinable from the amino acid sequence of the full-length form.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. Where the protein of the present invention is membrane-bound the present invention also provides for soluble forms of such protein. In such forms part or all of the domains of the protein causing the protein to be membrane bound are deleted such that the protein is fully secreted from the cell in which it is expressed.

Species homologs of the disclosed polynucleotides and proteins are also encompassed by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides.

Species homologs of the disclosed polynucleotides and proteins are also encompassed by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or is related to that encoded by the polynucleotides.

In particular embodiments, the isolated polynucleotides of the invention include, but are not limited to, a polynucleotide comprising the nucleotide sequence of SEQ ID NOS: 1-11.

The polynucleotides of the present invention also include the complement of any of the polynucleotides recited above.

The polynucleotides of the invention also provide polynucleotides including nucleotide sequences that are substantially equivalent to the polynucleotides recited above.

Polynucleotides according to the invention can have at least about 80%, more typically at least about 90% and even more typically at least about 95%, sequence identity to a polynucleotide recited above. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions, which can routinely isolate polynucleotides of the desired sequence identities.

A polynucleotide according to the invention can be joined to any of a variety of other nucleotide sequences by well-established recombinant DNA techniques well known in the art.

Useful nucleotide sequences for joining to polypeptides include an assortment of vectors, e.g., plasmids, cosmids, lambda phage derivatives, phagemids, and the like, that are will known in the art. Accordingly, the invention also encompasses any vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the sequence provided in SEQ ID NOS: 1-11 with a sequence from another isolate of the same species. Furthermore, to accommodate codon variability, the invention includes nucleic acid molecules coding for the same amino acid sequences, as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NOS: 1-11, or a fragment thereof. The recombinant constructs of the present invention comprise a vector, such as a plasmid or viral vector, into which a nucleic acid having the sequence of SEQ ID NOS: 1-11, or a fragment thereof is inserted, in a forward or reverse orientation. In the case of a vector comprising one of the ORFs of the present invention, the vector may further comprise regulatory sequences, including for example a promoter, operably linked to the ORF. For vectors comprising EMFs and/or UMFs, the vector may further comprise a marker sequence or heterologous ORF operably linked to the EMF or UMF. Large numbers of suitable vectors and promoters are known to those of kill in the art and are commercially available for generating the recombinant constructs of the present invention.

The isolated polynucleotide of the invention may be operably linked to an expression control sequence in order to produce the protein recombinantly. Many suitable expression control sequences are known in the art. As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers.

Generally, recombinant expression vectors will include origins of replication and selectable markers permitting transformation of the host cell, e.g., the ampicillin resistance gene of E. coli and S. cerevisiae TRP1 gene, and a promoter derived from a highly expressed gene to direct transcription of a downstream structural sequence. Such promoters can be derived from operons encoding glycolic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host.

The present invention further encompasses host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell, which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran-mediated transfection, or electroporation, procedures that are well known to those skill in the art. The host cells containing one of polynucleotides of the invention, can be used in conventional manners to produce the gene product encoded by the isolated fragment (in the case of an ORF) or can be used to produce a heterologous protein.

Any host/vector system can be used to express one or more of the ORFs of the present invention. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention.

Various mammalian cell culture systems can also be employed to express recombinant protein. Mammalian expression vectors will comprise an origin of replication, a suitable promoter and also any necessary ribosome binding sites, polyadenylation site, splice donor and acceptor sites, transcriptional termination sequences, and 5' flanking non-transcribed sequences.

Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein.

It may be possible to produce the protein in lower eukaryotes such as yeast or in prokaryotes such as bacteria. Potentially suitable yeast strains include *Saccharomyces cerevisiae, Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. Gene targeting can be used to replace a gene's existing regulatory region with a regulatory sequence isolated from a different gene or a novel regulatory sequence synthesized by genetic engineering methods.

Polypeptides of the Invention

The isolated polypeptides of the invention include, but are not limited to, a polypeptide comprising the amino acid sequence of SEQ ID NOS: 12-18. The polypeptides of the invention further include polypeptides which comprise one or more specific domains of the amino acid sequence in SEQ ID NOS: 12-15.

Protein compositions of the present invention may further comprise an acceptable carrier, such as a pharmaceutically acceptable, carrier.

The invention also relates to methods for producing a polypeptide comprising growing a culture of cells expressing sequences of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified. Preferred embodiments include those in which the protein produced by such process is a full length or mature form of the protein.

The invention further provides a polypeptide comprising an amino acid sequence that is substantially equivalent to SEQ ID NOS: 12-15. Polypeptides according to the invention can have at least about 95%, and more typically at least about 98%, sequence identity to SEQ ID NOS: 12-15. The present invention further encompasses isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence, but due to the degeneracy of the genetic code, encode an identical polypeptide sequence.

Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides.

Fragments are useful, for example, in generating antibodies against the native polypeptide. In an alternative method, the polypeptide or protein is purified from bacterial cells which naturally produce the polypeptide or protein. One skilled in the art can readily follow known methods.

The polypeptide can be expressed as a product of transgenic animals, modified in order to contain cells containing a nucleotidic sequence encoding for the protein.

Uses and Biological Activity

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

The use of the nucleotide and/or aminoacidic sequences (entire or their parts) can concern:

reagents and/or procedures to modulate cell death, in the therapy of pathologies that involve cell death, such as:
neoplasias;
degenerative disease in general, i.e. all those affections that involve a partial or total loss of the morphological and functional features typical of a cell, a tissue or an organ, so that vital functions are affected; for example: brain degenerative diseases, including Parkinson's diseases and other forms of dementia; degenerative diseases of skeletal muscles, including dystrophy, of heart, including myocardium dilating disease, and of other organs or tissues;
pathologies involving acute or chronic ischaemia of tissues;
pathologies involving excessive or deregulated inflammation, autoimmune diseases, multiple sclerosis, psoriasis, transplantation rejects or graft versus host disease;
hyperplasias (for example miointimal cell proliferation following angioplasty), dysplasias and similar diseases;
AIDS, tuberculosis or other infectious diseases involving apoptosis or cell death;
Other pathologies involving apoptosis or cell death;
reagents and/or procedures for modulating cell death in ageing;
reagents and/or procedures to preserve or reconstitute: cell compartments and/or tissues, such as in culturing progenitor and/or staminal cells to be used in haematology, oncology, transplantation and other medical fields; cells and tissues to be used in plastic and/or reconstructing surgery;
reagents and/or procedures to favour transplantation;
reagents and/or procedures to modulate cell survival and/or compartment size for cell systems to be used for laboratory work, scientific research and/or diagnostics. Reagents and procedures to modulate cell survival and/or death can also be in form of diagnostic kits (for diagnosis or prevention) including instructions for use.

Research Uses and Utilities

The polynucleotides provided by the present invention can be used by the research community for various purposes. The polynucleotides can be used to express recombinant protein for analysis, characterization, for staging of a disease or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent. (including labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

A protein, polypeptide or peptide of the present invention, or an agent based on AIR sequence or its parts (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

A therapeutically effective dose refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein or AIR-based agent of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection.

Alternately, one may administer the compound in a local rather than systemic manner, for example, via injection of the compound directly into arthritic joints or in fibrotic tissue, often in a depot or sustained release formulation. In order to prevent the scarring process frequently occurring as complication of glaucoma surgery, the compounds may be administered optically, for example, as eye drops. Furthermore, one may administer the drug in a targeted drug delivery system, for example, in a liposome coated with a specific antibody, targeting a specific tissue. The liposomes will be targeted to and taken up selectively by the afflicted tissue.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen. When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. When administered in liquid mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol.

When a therapeutically effective amount of protein or AIR-based agent of the present invention is administered by intravenous, cutaneous or subcutaneous injection, protein or AIR-based agent of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Several sustained-release materials have been established and are well known by those skilled in the art.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the proteinase inhibiting compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The amount of protein or AIR-based agent of the present invention in the pharmaceutical composition will depend upon the nature and severity of the condition being treated, and on the nature of prior treatments, which the patient has undergone. Ultimately, the attending, physician will decide the amount of protein of the present invention with which to treat each individual patient.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The therapeutic compositions are also presently valuable for veterinary applications. Particularly domestic animals and thoroughbred horses, in addition to humans, are desired patients for such treatment with proteins or AIR-based agents of the present invention. The dosage regimen of a pharmaceutical composition to be used will be determined by the attending physician considering various factors which modify the action of the agent, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins or AIR-based agents of the present invention in order to modulate cell survival or death or proliferation or to produce a desired effect on or activity in such cells. Treated cells can then be introduced in vivo for therapeutic purposes.

Methods for performing the uses listed above are well known to those skilled in the art. References disclosing such methods include without limitation: Maniatis T, Fritsch E F, Sambrook J. Molecular Cloning: a Laboratory Manual.II edition, Cold Spring Harbor, N.Y., USA, 1989.

Antibodies

Another aspect of the invention is an antibody that specifically binds the polypeptide of the invention. Such antibodies, in addition to those described, can be either monoclonal or polyclonal antibodies, as well fragments thereof and humanized forms or fully human forms, such as those produced in transgenic animals. The invention further provides two (one against peptides and the other against GST-Air protein) rabbit polyclonal and a mouse monoclonal antibodies according to the invention. Antibodies of the invention are useful for detection and/or purification of the polypeptides of the invention.

Polyclonal antibodies are produced by serial inoculations of peptides or polypeptides, or protein fused to GST (GST-protein) (such as GST-Air protein), in rabbits, followed by final boosting, rabbit blood drawing and serum testing for binding to the peptides, or polypeptides, or GST-protein with an appropriate test (for example, an immunoenzymatic test).

Monoclonal antibodies (mAb) are produced in our laboratory following the procedure cited in ref. 7.

Peptides useful for the production of rabbit antibodies against the protein are for example the following: SEQ ID NO 16: NSQNNFRNQYINNLKEIKS; SEQ ID NO 17:

KFYEKYRLDKIAETIYA; SEQ ID NO 18: NLKEEFEGK-NYLYPDAKD Furthermore, we produced also a polyclonal antibody against a GST-Air protein.

Diagnostic Assays and Kits

The present invention further provides methods to identify the presence or expression of one of the ORFs of the present invention, or homolog thereof, in a test sample, using a nucleic acid probe or antibodies of the present invention;

In general, methods for detecting a polynucleotide of the invention can comprise contacting a sample with a compound that binds to and forms a complex with the polynucleotide in conditions sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a peptide or polypeptide of the invention can comprise contacting a sample with a compound that binds to and forms a complex with the peptide or polypeptide in conditions sufficient to form the complex, and detecting the complex, so that if a complex is detected, a peptide or polypeptide of the invention is detected in the sample.

In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. The test samples of the present invention include, but are not limited to, cells, protein or extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing cell extracts are well known in the art and can be readily be adapted in order to obtain a sample which is compatible with the system utilized.

In another embodiment of the present invention, kits are encompassed which contain the necessary reagents to carry out the assays of the present invention. Specifically, the invention encompasses a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic, or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labelled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

Screening Assays

Using the isolated proteins and polynucleotides of the invention, the present invention further encompasses methods of obtaining and identifying agents which bind to a polypeptide encoded by the ORF from a polynucleotide with a sequence of SEQ ID NOS: 1-11, or to a specific domain of the polypeptide encoded by the nucleic acid, or to a nucleic acid with a sequence of SEQ ID NOS: 1-11. In detail, said method comprises the steps of: (a) contacting an agent with an isolated protein encoded by an ORF of the present invention, or nucleic acid of the invention; and (b) determining whether the agent binds to said protein or said nucleic acid. In general, therefore, such methods for identifying compounds that bind to a polynucleotide of the invention can comprise contacting a compound with a polynucleotide of the invention in conditions sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a peptide or polypeptide of the invention can comprise contacting a compound with a peptide or polypeptide of the invention in conditions sufficient to form peptide or polypeptide/compound complex, and detecting the complex, so that if a peptide or polypeptide/compound complex is detected, a compound that binds to a peptide or polypeptide of the invention is identified.

Methods for identifying compounds that bind to a peptide or polypeptide of the invention can also comprise contacting a compound with a polypeptide of the invention in a cell in conditions sufficient to form a polypeptide/compound complex, wherein the complex drives expression of a receptor gene sequence in the cell, and detecting the complex by detecting reporter gene sequence expression, so that if a peptide or polypeptide/compound complex is detected, a compound that binds a peptide or polypeptide of the invention is identified.

Compounds identified via such methods can include compounds which modulate the activity of a peptide or polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORFs of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, or pharmaceutical agents, or the like.

In addition, a skilled artisan can design sequence specific or element specific agents, modulating the expression of either a single ORF or multiple ORFs in AIR. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity. Antisense oligonucleotides complementary to AIR regions can also be designed. Triple helix-formation optimally results in a shut-off of RNA transcription from DNA, while antisense RNA hybridization blocks translation of an mRNA molecule into polypeptide. Both techniques have been demonstrated to be effective in model systems.

Information contained in the sequences of the present invention is necessary for the design of an antisense or triple helix oligonucleotide and other DNA binding agents. Agents which bind to a protein encoded by one of the ORFs of the present invention can be used as a diagnostic agent. Agents which bind to a protein encoded by one of the ORFs of the present invention can be formulated using known techniques to generate a pharmaceutical composition.

Use of Nucleic Acids as Probes

Another aspect of the subject invention is to provide for nucleic acid hybridization probes capable of hybridizing with naturally occurring nucleotide sequences. The hybridization probes of the subject invention may be derived from the nucleotide sequence of the SEQ ID NOS: 1-11. Any suitable hybridization technique can be employed. Any suitable hybridization technique can be employed, such as, for example, in situ hybridization. PCR provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. Fluorescent in situ hybridization of chromosomal preparations and other physical chromosome mapping techniques may be correlated with additional genetic map data. Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals. The nucleotide sequence may be used to produce purified peptides or polypeptides using well known methods of recombinant DNA technology. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the peptide or protein for purification and the availability of simplified purification procedures.

The present invention will be illustrated by the following examples and Figures which are not to be considered as limiting the scope of the invention.

EXAMPLES AND DETAILED DESCRIPTION OF THE FIGURES

Example 1

Identification of the novel sequence—To find novel elements that regulate apoptosis, we investigated a system of transfectants of the cell line Jurkat. These cells were stably transfected with a plasmid vector construct (pRC/CMV-Iκ-Balfa), expressing an inhibitor (Iκ-Balfa) of the transcription factors NF-κB; indeed, it is known that this inhibitor, blocking NF-κB activity, enhances cell apoptotic response, through mechanisms only partially understood. Control cells were transfected with the void vector (pRC/CMV). Stable transfectants were obtained by selection with geneticin (G418), 500 microgr/ml. We thus obtained two kinds of variants of a cell, one (IκBalfa+) of which displayed a block in NF-κB activation. Such block was revealed via either electrophoretic mobility shift assay (EMSA) and analysis of the expression of a reporter (CAT). For the electrophoretic mobility shift assay, cells were washed in phosphate-buffered saline (PBS) solution and pellet resuspended in a 20× volume of buffer for extracts (10 mM HEPES pH 7.9; 1.5 mM $MgCl_2$; 1 mM EDTA; 0.5 mM DTT; 0.5 mM PMSF; 10 mM KCl; 10% glycerol). To obtain nuclei, suspensions were passed through a 1 ml syringe and centrifuged at 1000 g for 5 mm; pellets were resuspended in a hypertonic solution and released nuclear proteins were obtained. Protein concentration was determined and such preparations were used for the electrophoretic mobility shift assays, using an NF-κB-binding (NF-κB oligo: 5'-CAACGGCAGGGGAATCTCCCTCTCCTT-3') (SEQ ID NO: 19) or a control (5'-CAACGGCAGGGGAATCTCCCTCTCCTT-3') (SEQ ID NO: 20) oligo. Double-stranded oligos were labelled with [gamma-32P] ATP (Amersham Corp.) using polynucleotide kinase (New England Biolabs, Beverely, Mass.). 5 micrograms of nuclear extracts were incubated in 20 microl of a buffer (10 mM Hepes ph 7.8, 50 mM KCl, 1 mM EDTA, 5 mM $MgCl_2$, 5 mM DTT, 10% glycerol, 0.7 mM PMSF, 2 micrograms poly [d (I-Cj), in the absence or presence of a 50 molar excess of unlabelled oligonucleotides for 15 mm at 4° C.; then the labelled oligo was added and, following a 30 mm incubation at room temperature, protein-DNA complexes were separated from the free probe on a 6% polyacrilamide gel and run in 0.25×Tris borate buffer at 200 V for 3 hours at room temperature. The gels were dried and exposed to X-ray film (Kodak AR). These experiments revealed the downmodulation of NF-KB nuclear levels, in TNF- or okadaic acid-stimulated IKBalfa+ cells, compared to wild type or control Jurkat cells. To functionally analyse NF-KB activity, cells were washed in PBS and resuspended at 106/ml in RPMI-20% FOS, in the presence of 50 micrograms/ml of a plasmid carrying a reporter gene (CAT) under the control of an enhancer containing an NF-KB consensus sequence; following a 10 mm incubation at 4° C., the cells were electropored (0.2 Ky, 960 microF) with a Bio-rad apparatus, washed, resuspended and cultured in RPMI-10% FCS. The subsequent CAT assay on cell extracts allowed to evaluate the NF-κB activity of the cells, and therefore to verify that TNF- or okadaic acid-stimulated licbalfa+ cells, compared to wild type or control Jurkat cells, showed markedly reduced levels of NF-κB activity. Due to this block in NF-KB activity, IKBalfa+ cells displayed a higher sensitivity to apoptosis. This was verified by analysis of apoptosis. Such analysis was performed by flow cytometry, according to the method described in ref. 2, using propidium iodide (PI) to label DNA in permeabilised cells. 5×10$^5$ cells were washed in PBS and resuspended in 1 ml of a solution containing 0.1% sodium citrate, 0.1% Triton-X-100, and 50 microgr/microl PI (Sigma Chem.); following a 30 mm incubation at 4° C. in the dark, cell nuclei were analysed with a Becton-Dickinson FACScan flow cytometer using the Lysis 1 program. Cellular debris was excluded from analysis by raising the forward scatter threshold, and the DNA content of the nuclei was registered on a logarithmic scale. The percentage of the cells in the hypodiploid region was calculated. These experiments allowed to determine that, following stimulation with TNF or okadaic acid, IKBalfa+ cells, compared to wild type or control Jurkat cells, displayed higher apoptosis levels.

We stimulated the two cell types with an apoptosis inducer: okadaic acid, extracted RNA, obtained corresponding cDNAs and compared these by a differential display approach (ref. 3). In particular, IκBalfa+ and control (pRC/CMV) cells were incubated with 70 ng/ml okadaic acid (Sigma) for 8 h, then RNA was extracted and treated with DNAse I (Message Clean, GenHunter Corporation) for removing contaminating DNA. CDNA was then obtained using a reverse transcriptase with HT11-G oligos (where H is the AAGCTT restriction sequence specific Hind III). The cDNA was amplified by PCR using HT11-G as first and H-AP7 (5'AAGCTTAACGAGG3') (SEQ ID NO: 21) as second oligo, in the presence of alpha 32PdATP, following the protocol indicated GenHunter Corporation (RNA Image, GenHunter Corporation). These amplified products were run on a 6% polyacrilamide denaturing gel; this was blotted onto 3M paper, dried and exposed to X-ray film (Kodak AR) for 72 h at −80° C. A resulting band of about 500 bp, selectively present in the cDNA from IκBalfa+ cells, was identified and eluted from the corresponding gel. This cDNA was re-amplified and cloned in pGEM-Teasy, to be sequenced and used as a probe in Northen blot assays.

Following these procedures we could produce and identify a cDNA, corresponding to a mRNA expressed selectively in IκBalfa+ cells.

This cDNA represented a fragment of the corresponding mRNA. To obtained the full-length cDNA, we constructed, from okadaic acid-stimulated IκBalfa+ Jurkat cells, a cDNA library in Uni-ZAP XR vector and screened such library using the above described cDNA obtained by differential display (4). We therefore obtained and sequenced the full-lenght cDNA (SEQ ID NO 1). We subsequently named such sequence AIR (Apoptosis-Induced and Regulator).

Example 2

Analysis of sequence expression in human cells—Subsequent experiments were performed by Northern blot, following standard procedures described in ref. 5. 30×10$^6$ cells were washed and the pellet resuspended in 3 ml of Trizol reagent (Life Technologies). RNA was extracted, quantified by calculating OD at 260 nm and normalised by gel electrophoresis. 30 micrograms of RNA for each sample were run on an 1% agarose gel containing 2.2 M formaldehyde and blotted on a nylon support (Hybond, Amersham). Filters were UV-crosslinked and hybridized with an [alfa-$^{32}$P]ATP-labelled probe corresponding to SEQ ID NO 1. These experiments revealed that this cDNA that we obtained (SEQ ID NO 1) specifically detected a mRNA, expressed in cells stimulated with apoptosis-inducing agents. Indeed, as it is showed in FIG. 1, this mRNA is induced in Jurkat cells by stimulation via Fas.

Figure 1B:
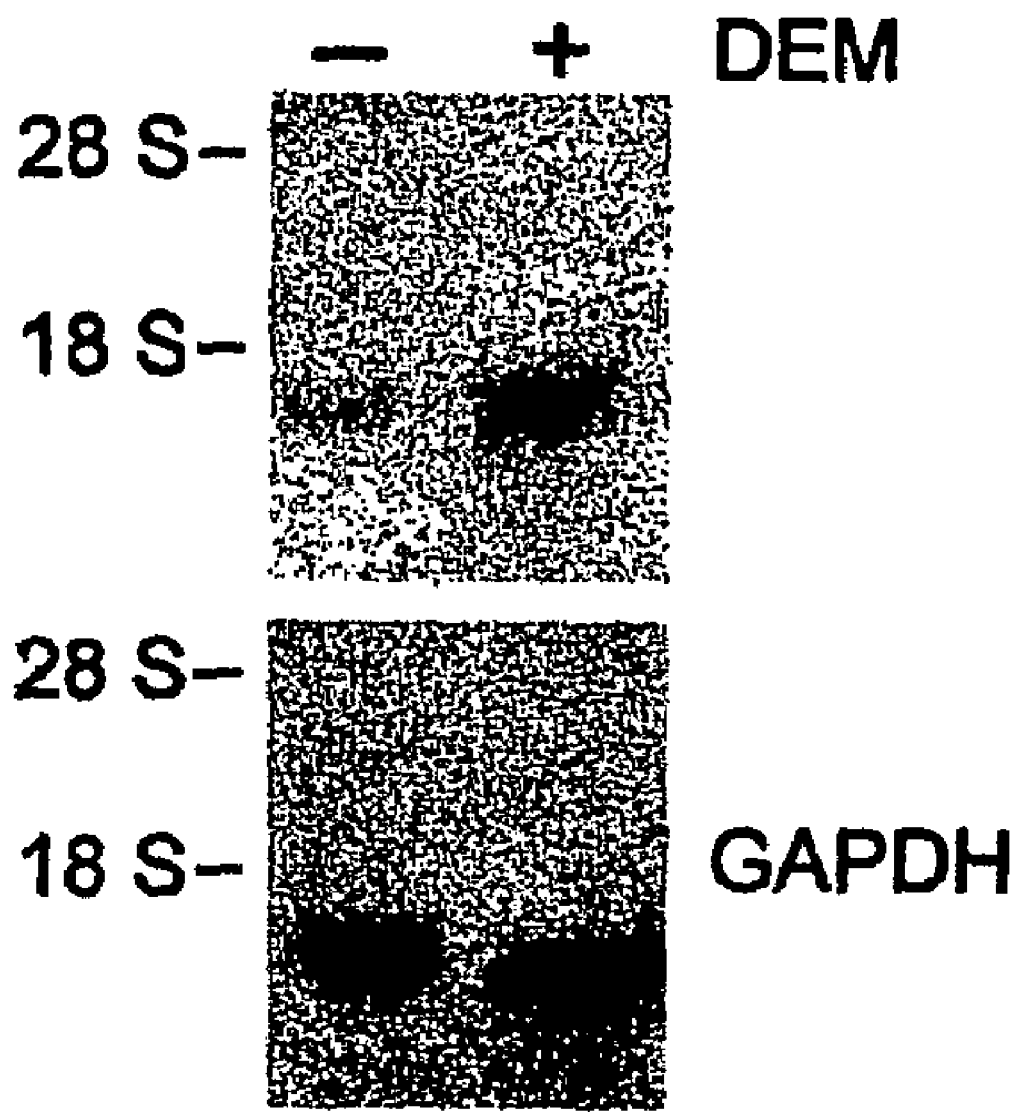
FIG. 1B—Expression of the sequence of SEQ ID NO 1 in human cells. (B panel) Northern blot of mRNA from SH-SY5Y unstimulated (−) or stimulated with diethylmaleate (DEM) (+).GAPDH gene expression is shown for comparative purposes.

Furthermore, in SH-SY5Y neuroblastoma cells, the mRNA identified by our cDNA is not or poorly expressed in basal conditions, while it is markedly expressed following stimulation with the apoptosis inducer diethylmaleate (DEM) (FIG. 1).

Molecular biology standard procedures followed in this experimental work are described in detail in ref. 4.

Example 3

Novel proteins, encoded by AIR sequence6—On the basis of AIR sequence, we designed three epitopes (SEQ ID NOS: 16-18) of the corresponding protein (that we named Air: comprising SEQ ID NO 13), and furthermore we obtained, by cloning of the sequence in a PET22 vector (ref. 4), the recombinant protein. Following methodologies well known to those skill in the art, we obtained rabbit specific polyclonal antibodies that we used for immunoprecipitation experiments in extracts from Fas-stimulated Jurkat cells. 3×10$^6$ cells were incubated with the anti-Fas antibody CH-11 (50 ng/ml) at 37° C. in a 5% C02 atmosphere for 2 hours in medium methionine free. Then 35S—methionine (100 microCi) was added to the cells. After 12 hours cell were lysated and the proteins obtained (500 microgr) were immunoprecipitated with a rabbit anti-Air polyclonal antibody and Proteina A-Sepharose (LKB-Pharmacia). The immunocomplexes were run on a SDS-PAGE 14% polyacrilamide gel. The gel was dried and exposed to X-ray film. These experiments revealed native Air (FIG. 2).

Figure 2:
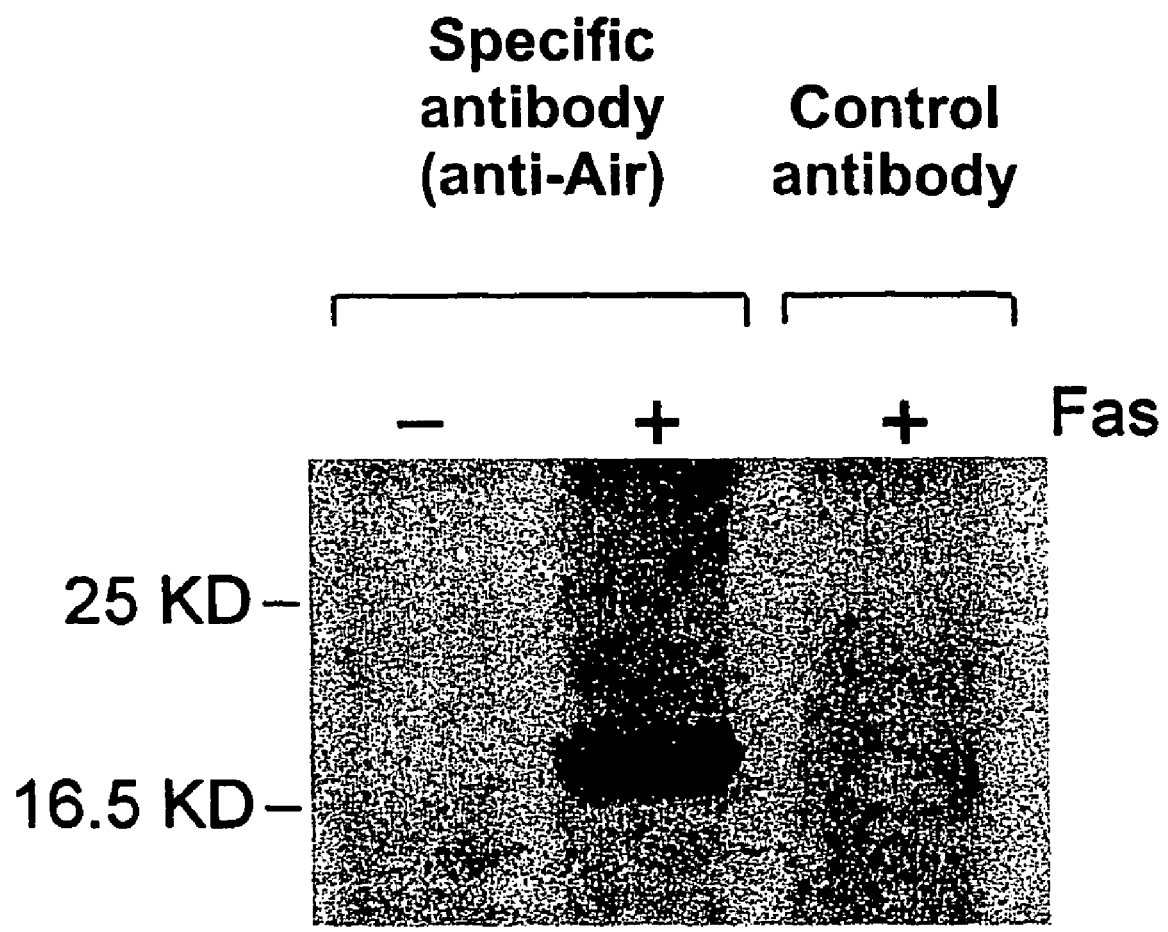
FIG. 2—A protein (Air) encoded by the sequence of SEQ ID NO 1 (A panel) Immunoprecipitation of the protein with antibodies (anti-Air polyclonal antibodies) from extracts of Jurkat cells unstimulated or stimulated with the anti-Fas mAb CH-11.
Figure 3A:
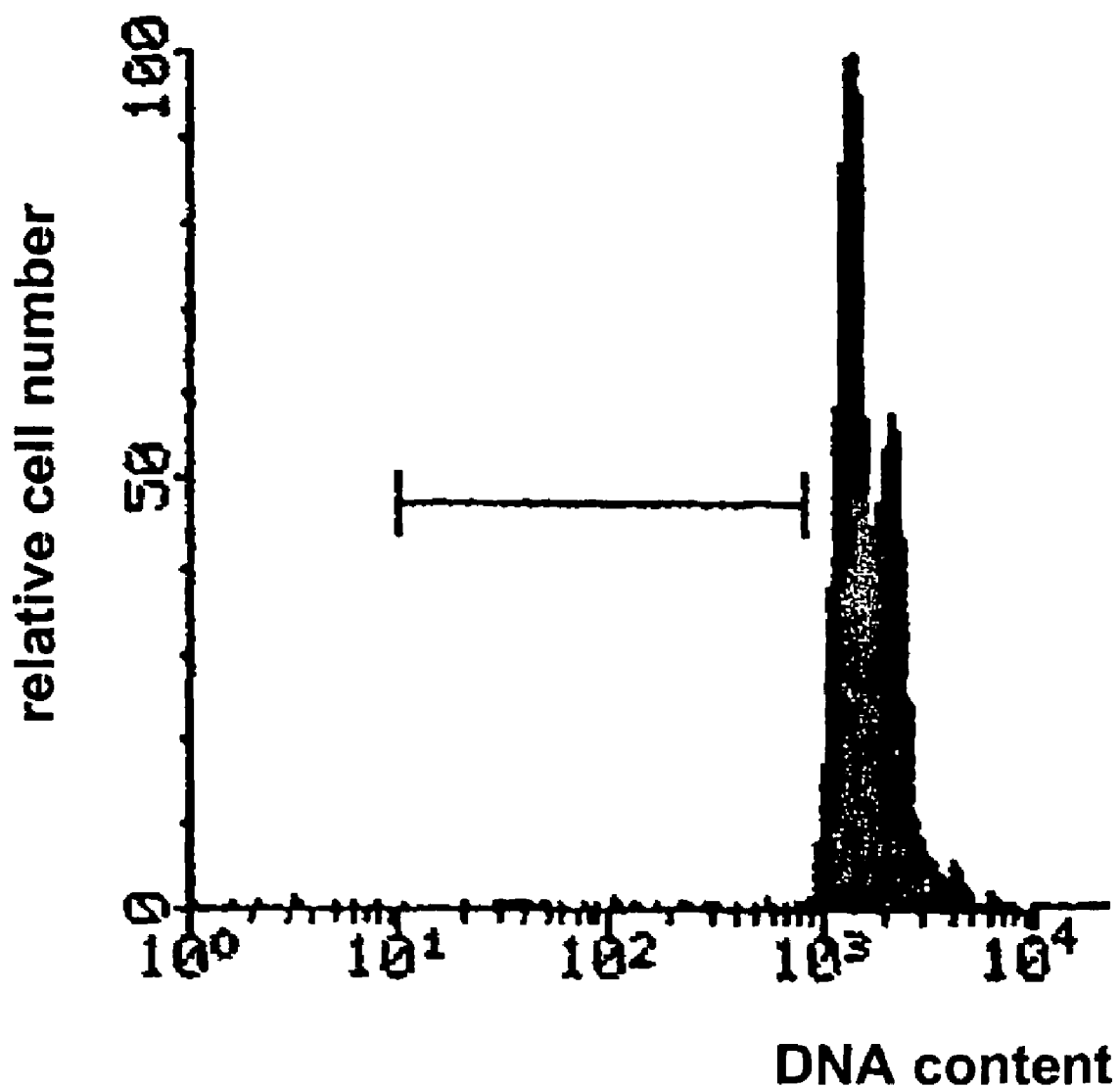
FIG. 3A—Apoptosis inhibition by using antisense oligonucleotides in SH-SY5Y cells. (A panel): cells incubated in control medium.
Figure 3B:
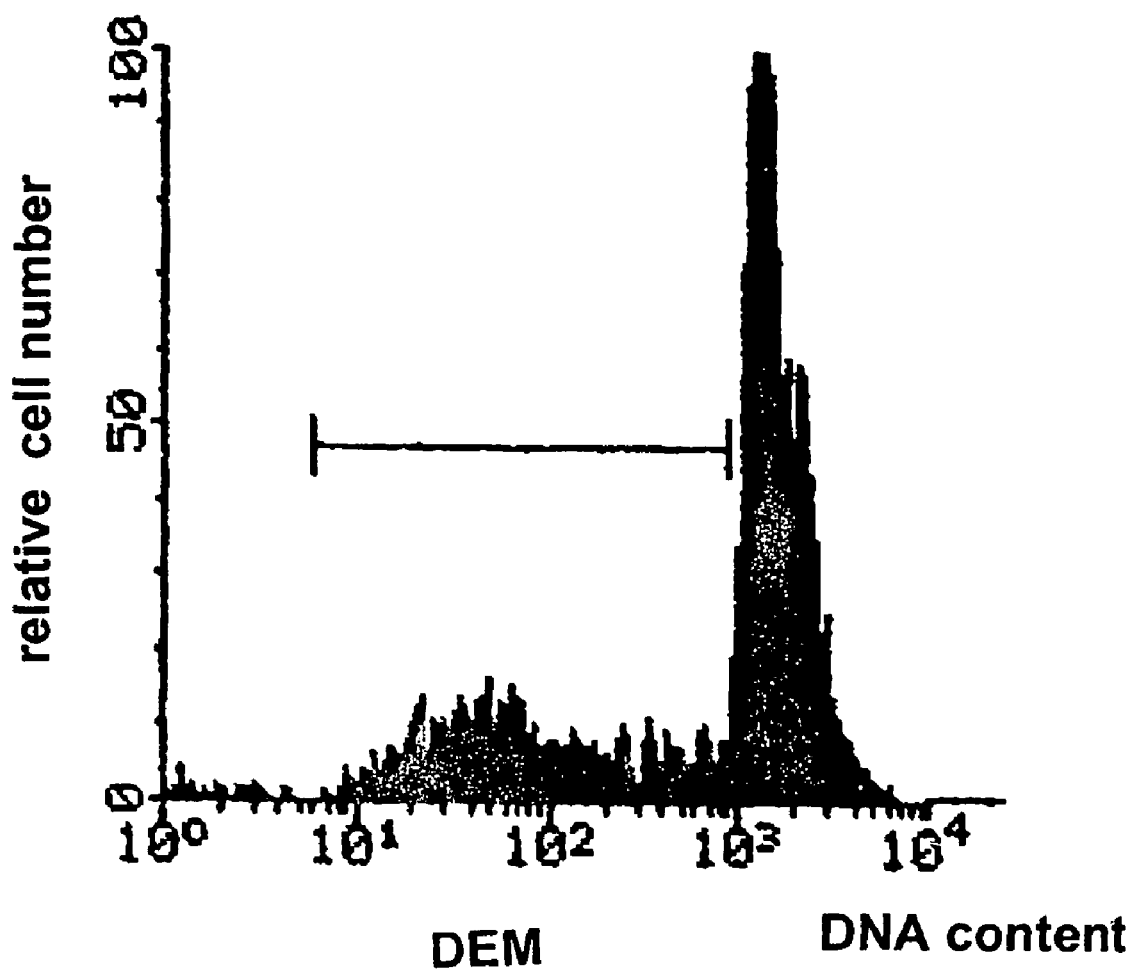
FIG. 3B—Apoptosis inhibition by using antisense oligonucleotides in SH-SY5Y cells. (B panel): cells incubated with DEM.
Figure 3C:
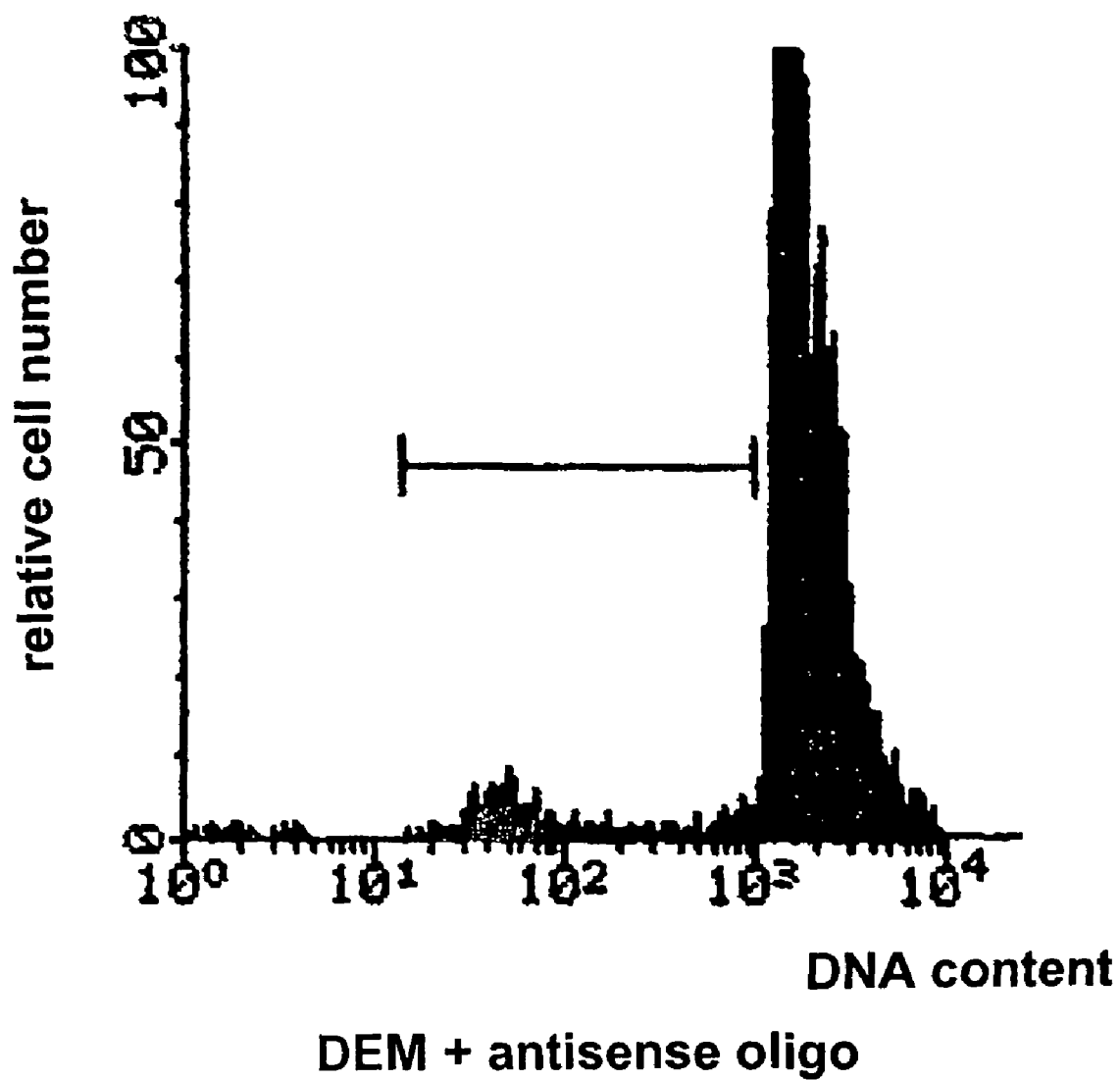
FIG. 3C—Apoptosis inhibition by using antisense oligonucleotides in SH-SY5Y cells. (C panel): cells incubated with DEM+ antisense oligo.
Figure 3D:
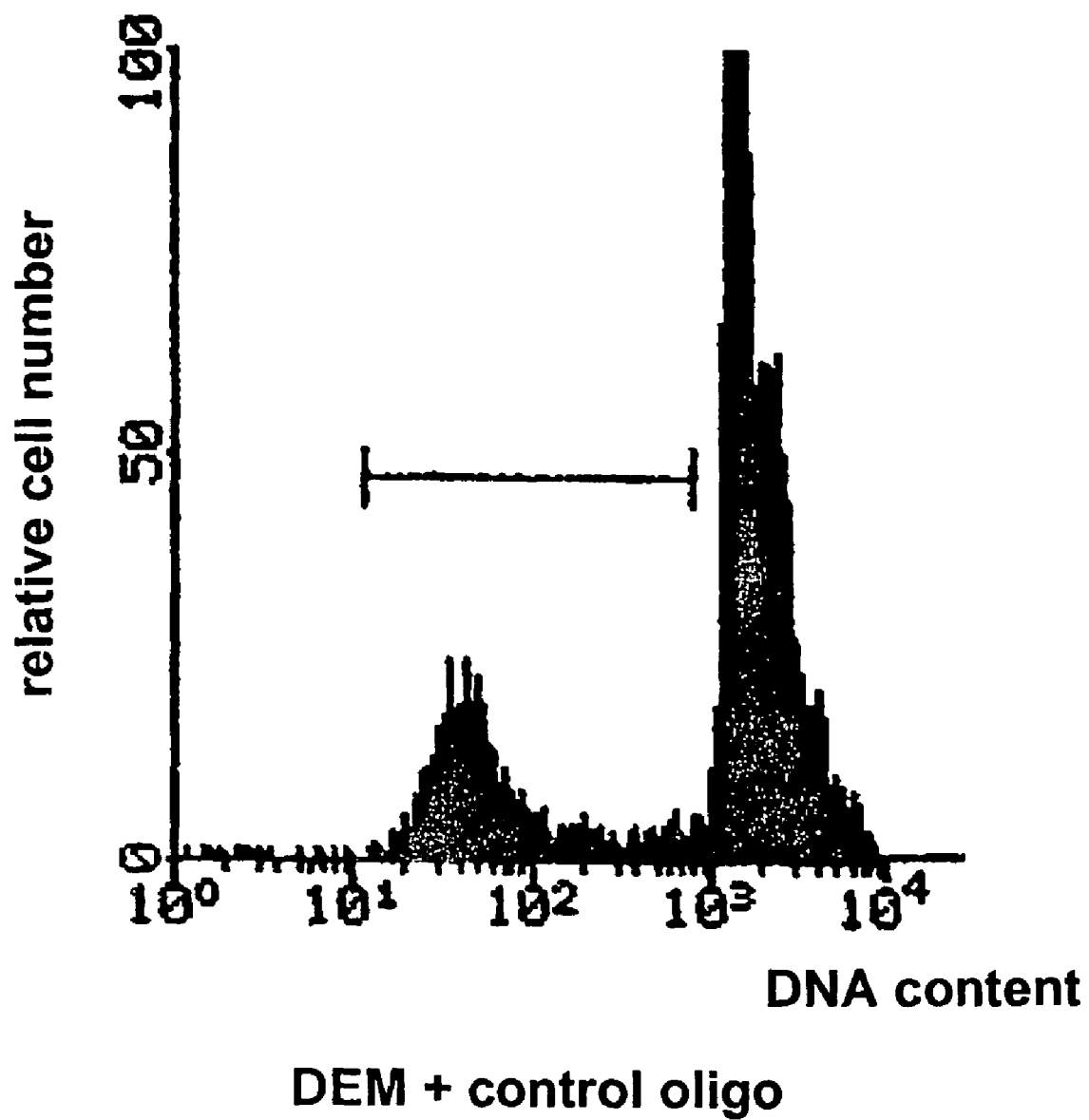
FIG. 3D—Apoptosis inhibition by using antisense oligonucleotides in SH-SY5Y cells. (D panel): cells incubated with DEM+ control oligo.

As shown in FIG. 2, the presence of the protein has been analysed in extracts from Jurkat cells either unstimulated (−) or stimulated with the anti-Fas mAb CH-11.

In addition, by sequence analysis we identified that other polypeptides can be encoded by AIR sequence or its possible variants or parts (specifically, SEQ ID NOS 2, 4 and 5) and correspond to SEQ ID NO 12, SEQ ID NO 14 and SEQ ID NO 15.

Example 4

Modulation of apoptosis—We investigated whether the cDNA and protein that we identified were able to modulate apoptosis To this purposes, we designed, in a first and a second sets of experiments, antisense phosphorothioate oligonucleotides (SEQ ID NOS: 6, 7, 8) directed at blocking Air synthesis. Control (nonsense) oligonucleotides were also designed (SEQ ID NOS: 9, 10, 11). Any of the three antisense oligonucleotides were able to modulate apoptosis, in this case, by blocking it (FIGS. 3, 4, 5 and 6). These findings demonstrate that: 1) the mRNA and protein that we identified regulate apoptosis; 2) by acting on them, specifically with any one of the three antisense (SEQ ID NOS: 6, 7, 8), but also possibly with any other eventual reagent based on AIR or Air sequences (that we identified and for which we found a specific property and utilization), it is possible to modulate apoptosis, i.e. to perform an utilization for modulating cell death.

Example 5

Presence of the Protein in primary ex vivo cells—We investigated whether our protein was present in primary ex vivo cells. (Procedures and conditions for isolation and culturing of primary cells are described in ref. 8-10). To this purpose, we first analysed three samples of B chronic lymphocytic leukemia (B-CLL) cells, since these cells can be considered a primary counterpart of the cell line that we initially studied. To detect the protein, we perform intracellular immuno-fluorescence experiments. $1-2 \times 10^6$ cells were fixed and permeabilised with 250 microl of Cytofix/Cytoperm (Pharmingen) solution, then incubated with the specific anti-Air rabbit polyclonal or a control rabbit antibody, followed by washing with Perm/Wash (Pharmingen) and a second incubation with fluorescein isothiocyanate (FITC)-conjugated goat anti-rabbit antibody. Then the cells were analysed with a FACScan (Becton Dickinson) flow cytometer. These experiments allowed to detect the presence of the protein in the three analysed B-CLL samples (FIGS. 7, 8 and 9).

Figure 7A:
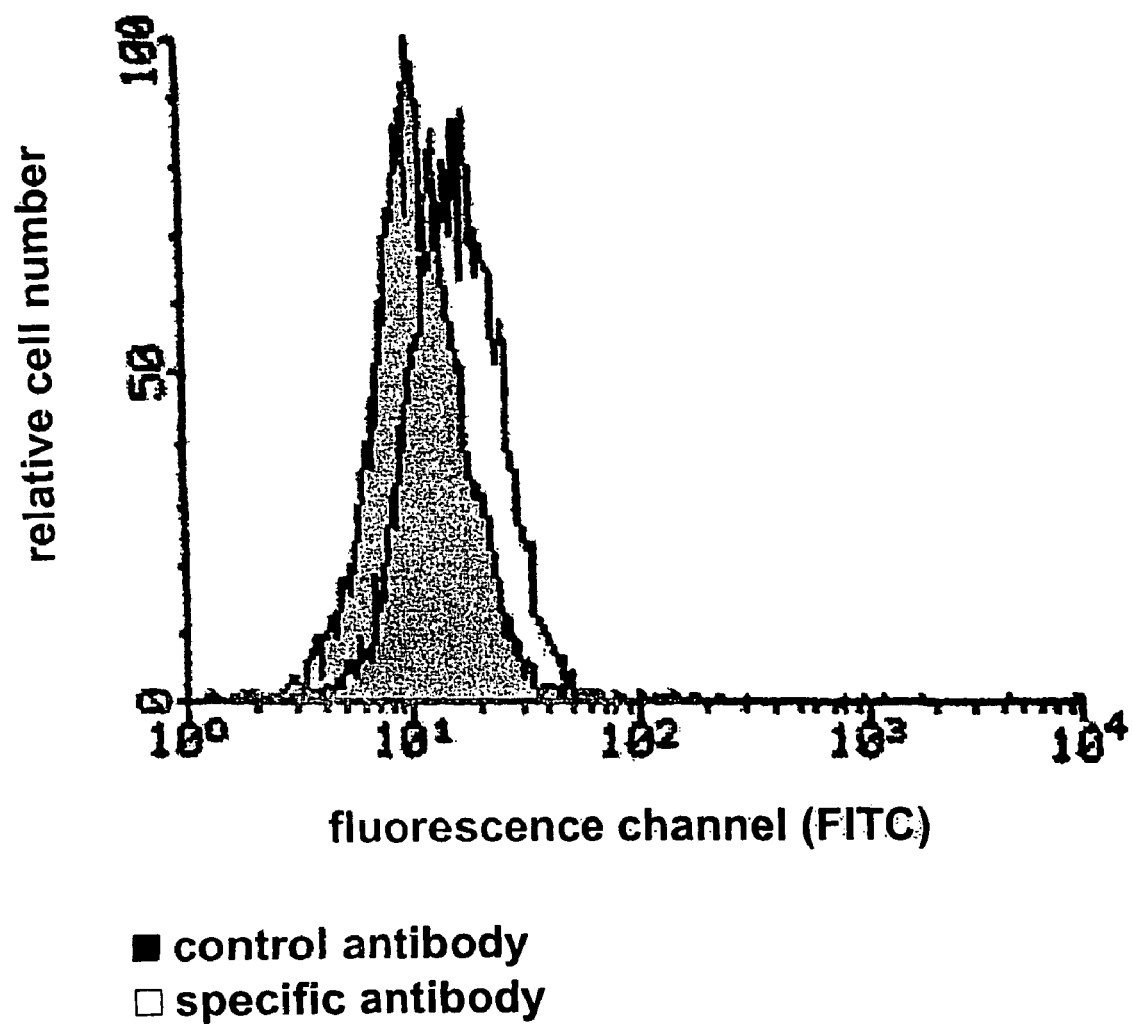
FIG. 7A—Intracellular expression of Air protein in primary cells from a patient affected by chronic lymphocytic leukemia (B-CLL). (A panel): unstimulated cells.
Figure 7B:
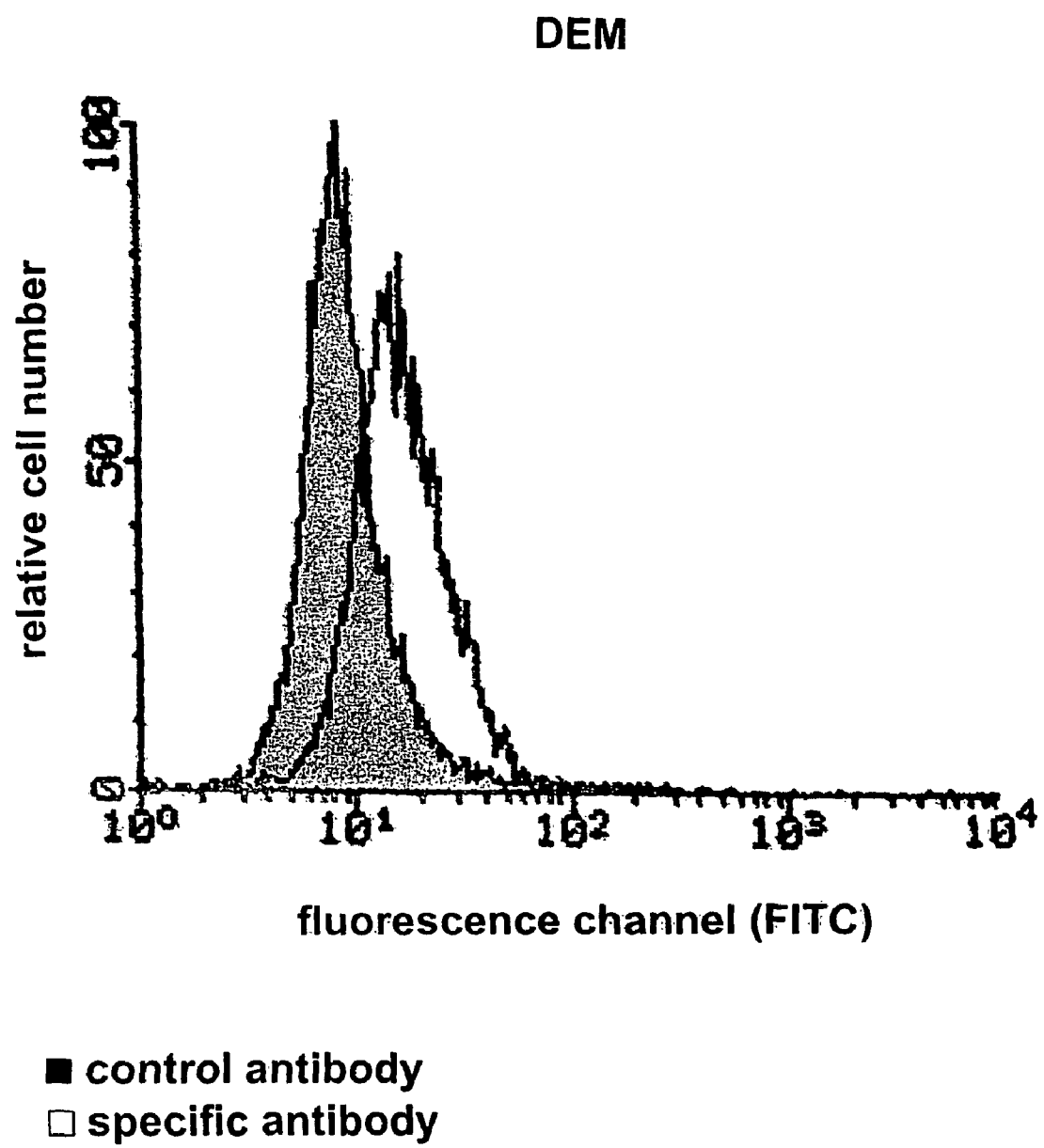
FIG. 7B—Intracellular expression of Air protein in primary cells from a patient affected by chronic lymphocytic leukemia (B-CLL). (B panel): DEM-stimulated cells.
Figure 8A:
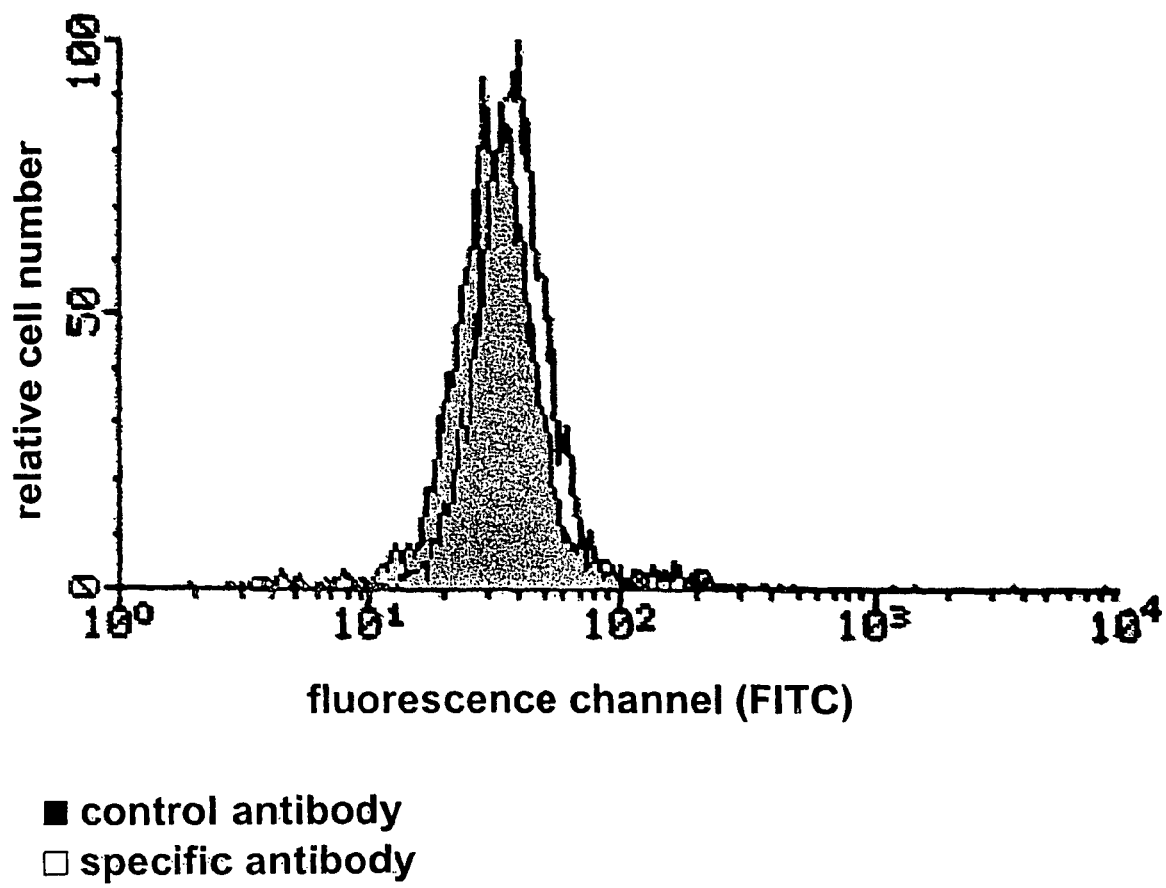
FIG. 8A—Intracellular expression of Air protein in primary cells from a patient affected by B chronic lymphocytic leukemia (B-CLL). (A panel): unstimulated cells.
Figure 8B:
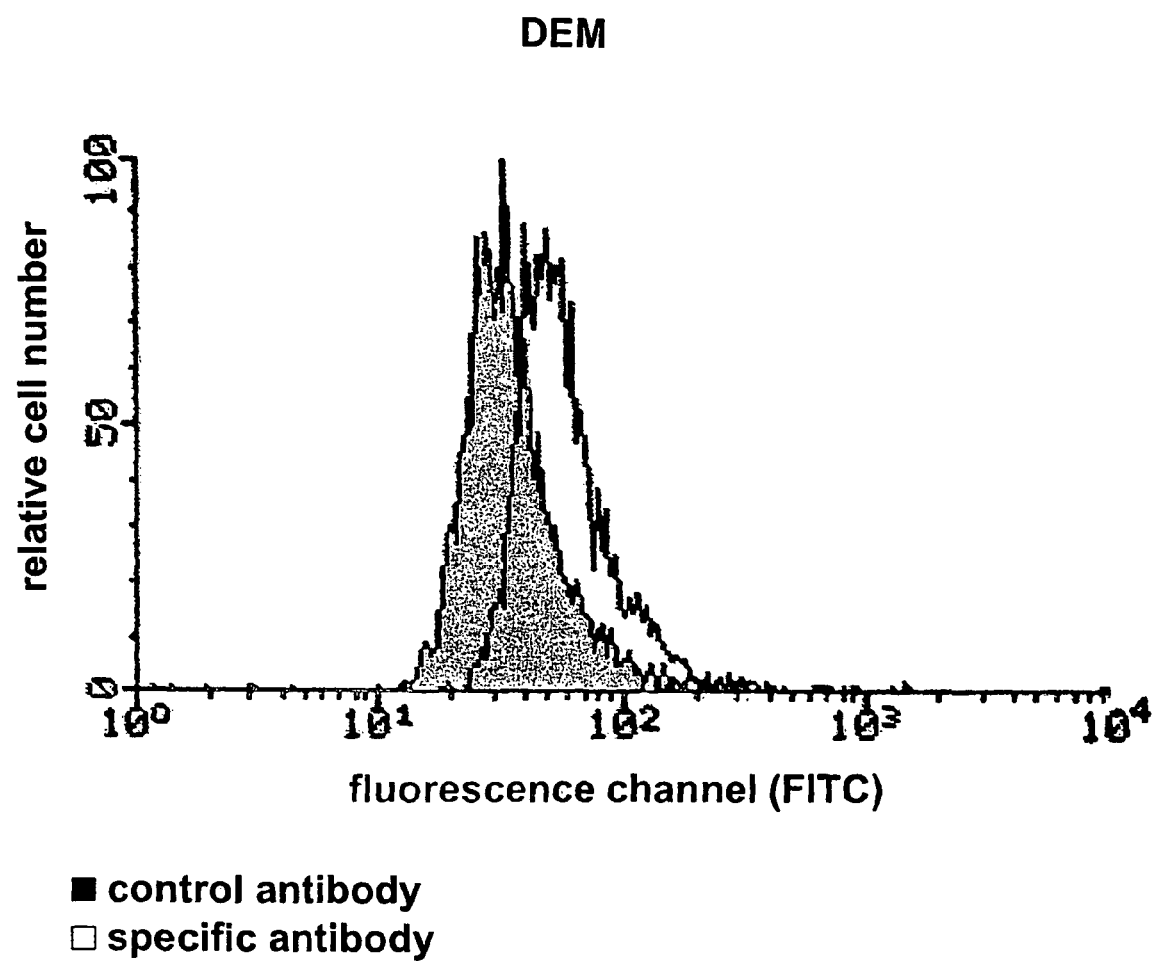
FIG. 8B—Intracellular expression of Air protein in primary cells from a patient affected by B chronic lymphocytic leukemia (B-CLL). (B panel): DEM-stimulated cells.
Figure 8C:
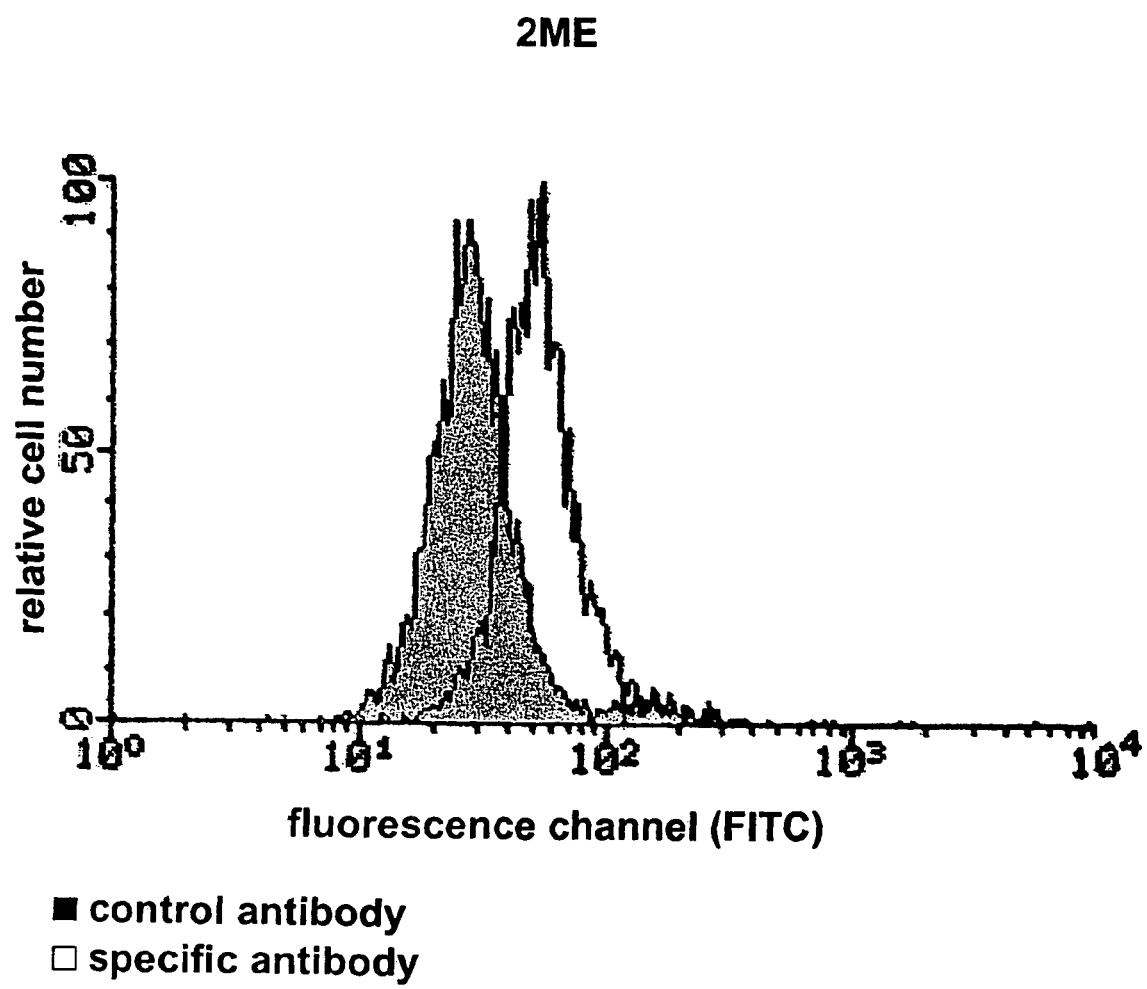
FIG. 8C—Intracellular expression of Air protein in primary cells from a patient affected by B chronic lymphocytic leukemia (B-CLL). (C panel): cells stimulated with the drug 2-Methoxymethylestradiol (2-ME).
Figure 9A:
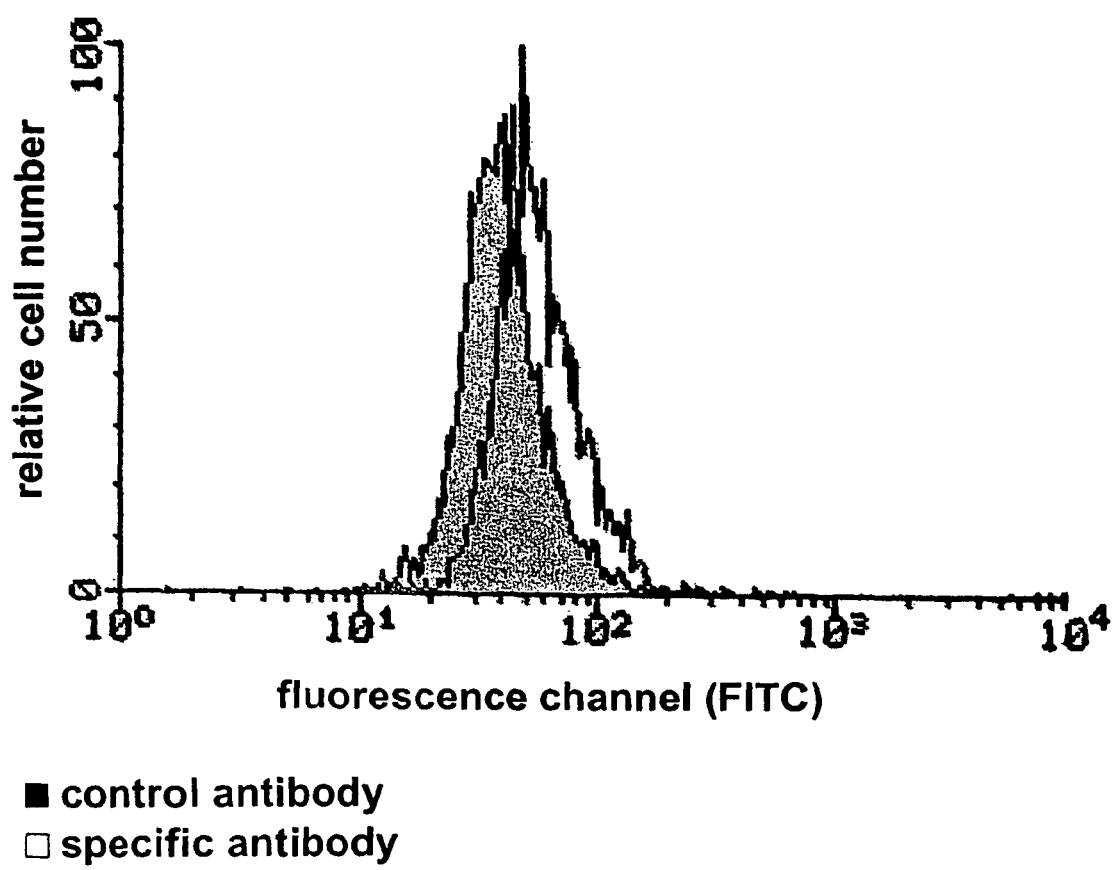
FIG. 9A—Intracellular expression of Air protein in primary cells from a patient affected by B chronic lymphocytic leukemia (B-CLL). (A panel): unstimulated cells.
Figure 9B:
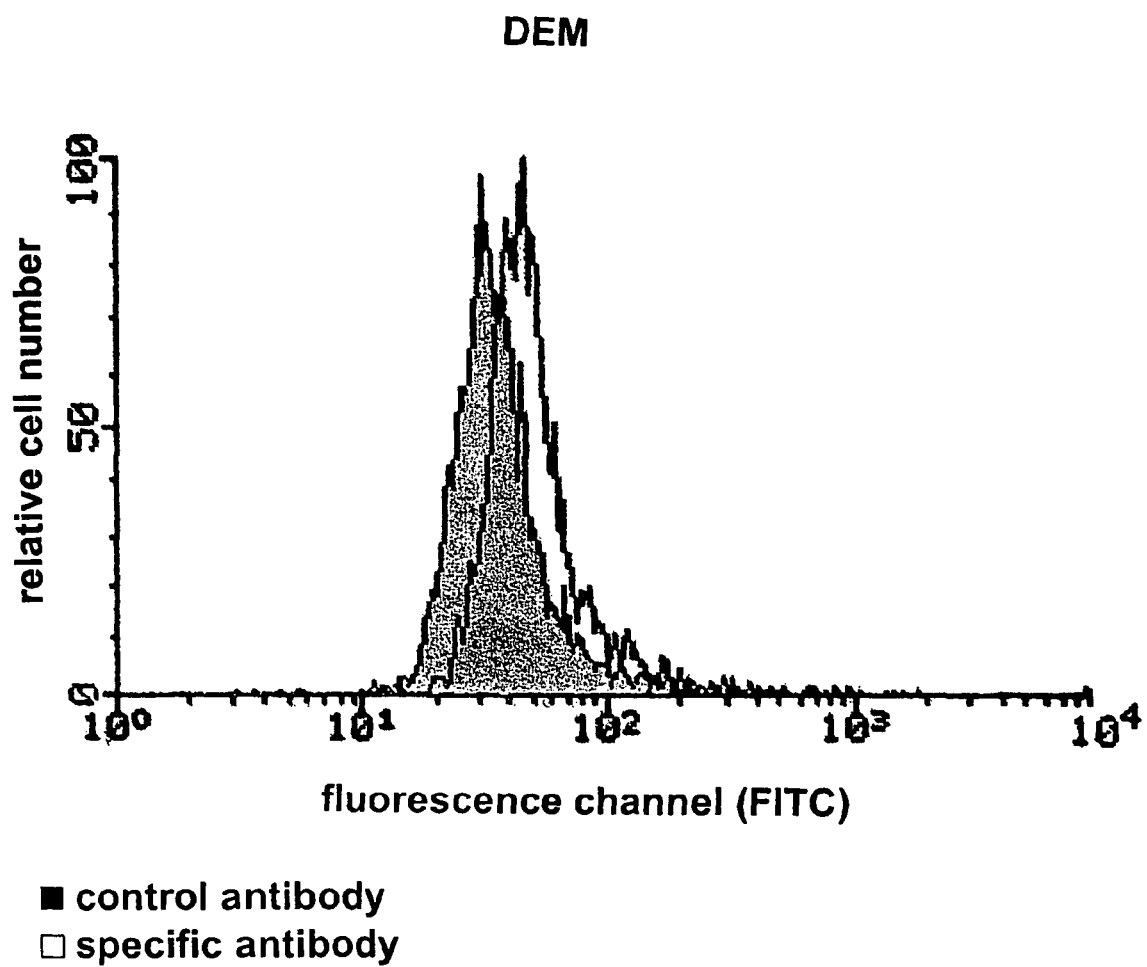
FIG. 9B—Intracellular expression of Air protein in primary cells from a patient affected by B chronic lymphocytic leukemia (B-CLL). (B panel): DEM-stimulated cells.
Figure 9C:
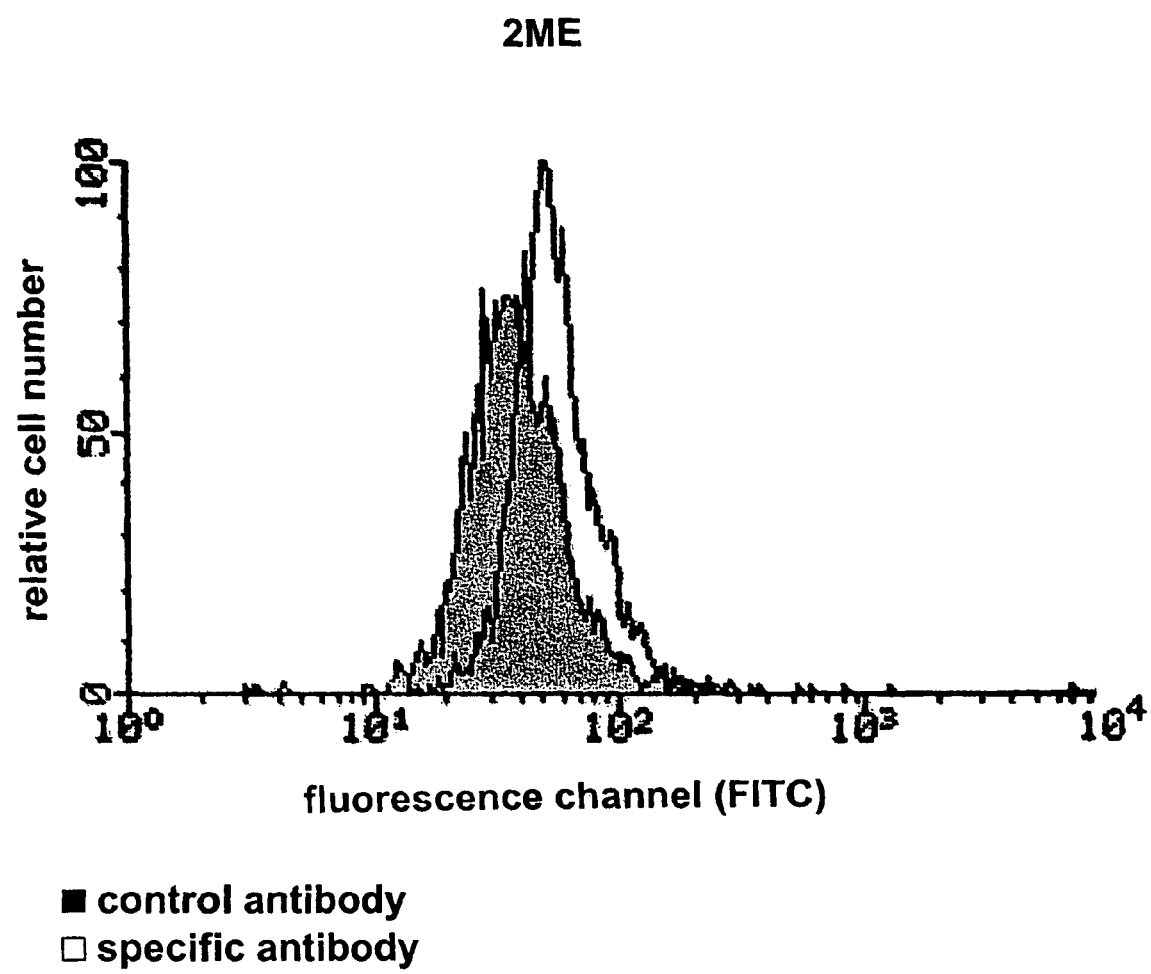
FIG. 9C—Intracellular expression of Air protein in primary cells from a patient affected by B chronic lymphocytic leukemia (B-CLL). (C panel): cells stimulated with the drug 2-Methoxymethylestradiol (2-ME).

The three B-CLL samples analysed in FIGS. 7, 8 and 9 were biologically different, i.e. obtained from three different patients affected by the same type of pathology.

Example 6

Figure 10:
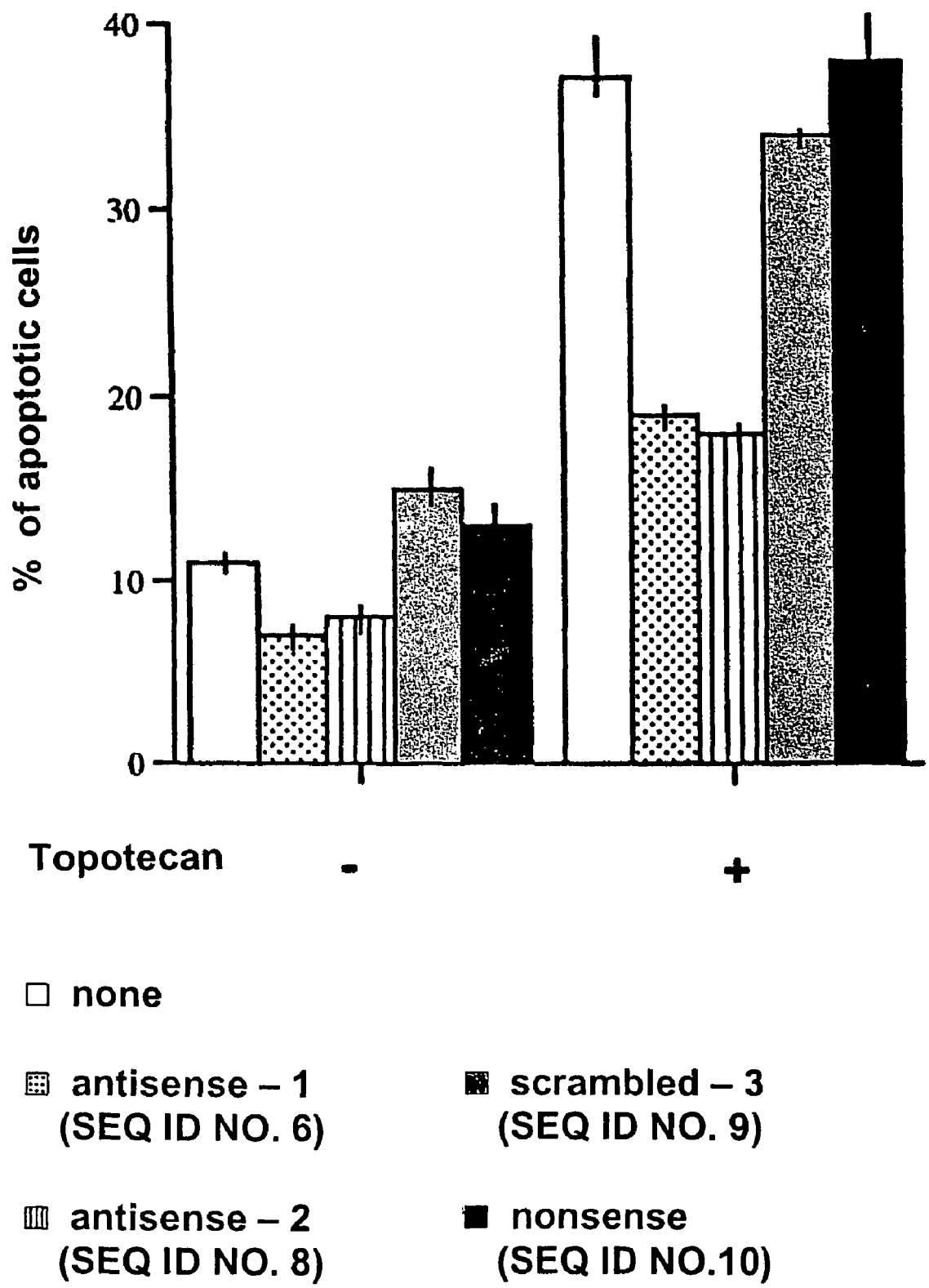
FIG. 10—Effect of antisense oligonucleotides on primary myeloblastic leukemia (AML) cell apoptosis induced by 50 ng/ml of topotecan, an inhibitor of topoisomerase.

Modulation of apoptosis in primary ex vivo cells—To investigate whether our protein modulated apoptosis in primary ex vivo cells, we analysed the effect of antisense oligonucleotides that block the protein synthesis. Such effect has been analysed in cells of acute myeloblastic leukemia (AML), obtained from patient's peripheral blood and incubated with a drug used in the therapy of such kind of pathology: the topoisomerase inhibitor topotecan, that is an apoptosis inducer. While control oligos did not have any effect on cell apoptosis, antisense oligos markedly blocked it, as illustrated in FIG. 10. These findings indicate that our protein regulates apoptosis in primary human cells, and that by acting on it we can modulate cell death.

In conclusion, AIR cDNA, detected in TNF-α stimulated Jurkat transfectants with suppression of NF-κB/Rel activity, corresponded to a full-lenght sequence of >3500 bp. We subsequently found that AIR message was expressed in some cell lines (Jurkat, HeLa, SH-SY-5Y neuroblastoma) and primary human cells (human peripheral blood T lymphocytes and monocytes) upon treatment with apoptosis inducers that do not simultaneously stimulate NF-κB/Rel activity, including Fas ligand in Jurkat and oxidative stress inducers (diethylmaleate, DEM) in HeLa cells and in human normal peripheral blood lymphocytes and monocytes. Importantly, AIR was expressed in primary myeloblasts from patients affected by AML.

Figure 17:
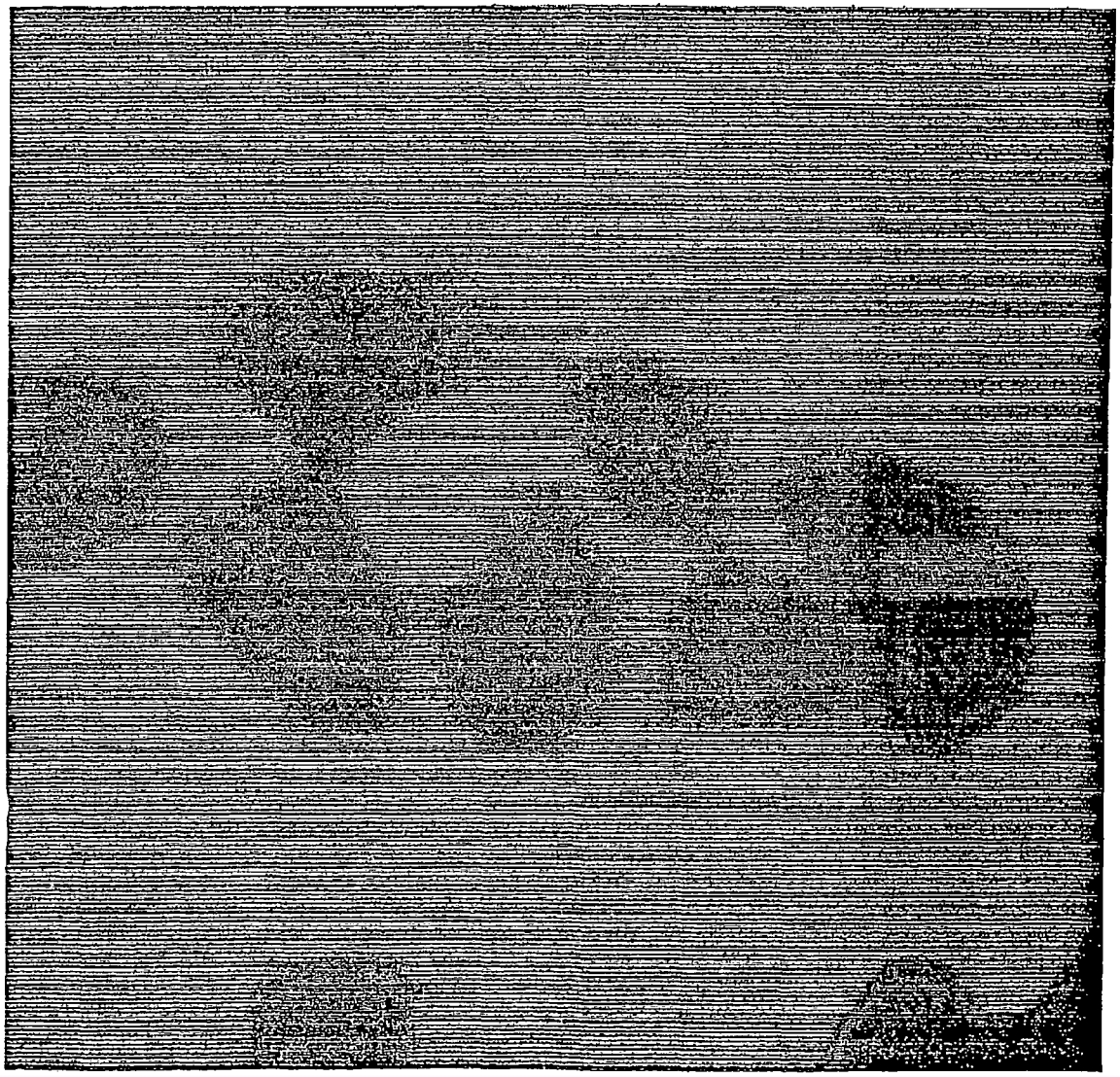
FIG. 17—Staining of HeLa cells with anti-Air polyclonal antibodies.

We identified four possible ORFs, encoding for polypeptide sequences, and particularly ORF2, encoding a protein that we subsequently named Air (SEQ ID NO: 13) Furthermore, other polypeptides can be encoded by AIR sequence or its parts, and correspond to SEQ ID NO 12, SEQ ID NO 14 and SEQ ID NO 15. We first produced a rabbit polyclonal antibody against three epitopes of Air putative protein. Such antibody immunoprecipitated from Fas-stimulated Jurkat cell extracts a protein with a corresponding m.w. (FIG. 2). We then produced a GST-Air protein and raised a new polyclonal rabbit antibody. The antibody specifically recognised a target protein in HeLa cells (FIG. 17). Other localizations of the protein are possible in different cell types, or in cells in a different physiologic or pathologic status.

To analyse Air protein involvement in apoptosis, we designed three different antisense oligonucleotides and three control oligos, and tested their effect on Air expression and cell apoptosis. The specific AIR antisense oligonucleotides downmodulated Air protein levels, analysed by flow cytometry, in Jurkat cells (FIG. 11) and in primary AML cells (FIG. 10). The addition of the antisense oligos remarkably downmodulated apoptosis, measured as caspase 3 activity, mitochondrion depolarization, annexin V binding and hypodiploid cell apoptosis, in Fas- or DEM-stimulated Jurkat cells, neuroblastoma SH-SH-5Y cells, DEM-stimulated normal human peripheral blood (ex vivo) T lymphocytes and monocytes, and in cytosine arabinoside (AraC)-stimulated primary (ex vivo) AML blasts (FIGS. 10-16).

These results demonstrate a role for AIR sequence and Air protein in the apoptotic process of human primary normal and neoplastic cells. Modulation of AIR expression can interfere with cell survival and/or death.

Molecular biology standard procedures followed in this experimental work are more exaustively described in ref. 4, while isolation and culturing methods employed for primary cells are described in details in our papers cited in ref. 8-10. Finally, by following standard procedures, already performed in our laboratory (7), we produced a murine monoclonal antibody, named 2002-1. This is specific for a polypeptide encoded by a part of AIR sequence.

DETAILED DESCRIPTION OF THE FIGURES

FIG. 1—Expression of AIR in human cells. A panel: Jurkat wild type cells were incubated with the anti-Fas antibody CH-11 (50 ng/ml) in 10% FCS RPMI at 37° C. in a 5% C02 atmosphere for the indicated times. Then RNA was obtained and the presence of AIR mRNA was detected by Northern blot analysis. GAPDH gene expression is shown for comparative purposes. B panel: SH-SY-5Y cells lines were incubated in the presence of diethylmaleate (DEM) (1 mM) in 10% FCS RPMI at 37° C. in a 5% C02 atmosphere for 6 hours. Then RNA was obtained and the presence of AIR mRNA was detected by Northern blot analysis. GAPDH gene expression is shown for comparative purposes.

FIG. 2. Immunoprecipitation of Air protein from extracts of Fas-stimulated Jurkat cells. A panel: Jurkat cells were incubated with the anti-Fas antibody CH-11 (50 ng/ml) at 37° C. in a 5% C02 atmosphere for 2 hours in medium methionine-free. Then 35S-methionine (100 microCi) was added to the cells. After 12 hours cell were lysated and the proteins obtained (500 microgr) were immunoprecipitated with a rabbit anti-Air polyclonal antibody and Protein A-Sepharose (LKB-Pharmacia). The immunocomplexes were run on a SDS-PAGE 14% polyacrilamide gel. The gel was dried and exposed to X-ray film. B panel: aminoacid sequence of Air protein.

FIG. 3—Apoptosis inhibition with antisense oligonucleotides in SH-SY5Y neuroblastoma cells. $3\times10^5$ cells were incubated at 37° C. in a 5% $CO_2$ atmosphere, in the absence or absence of 2 mM DEM and antisense or control oligonucleotides (7 microM). After 16 h, apoptosis was analysed as described in the text. Analogous results were obtained with any of the three antisense and the three control oligonucleotides, respectively.

Figure 4:
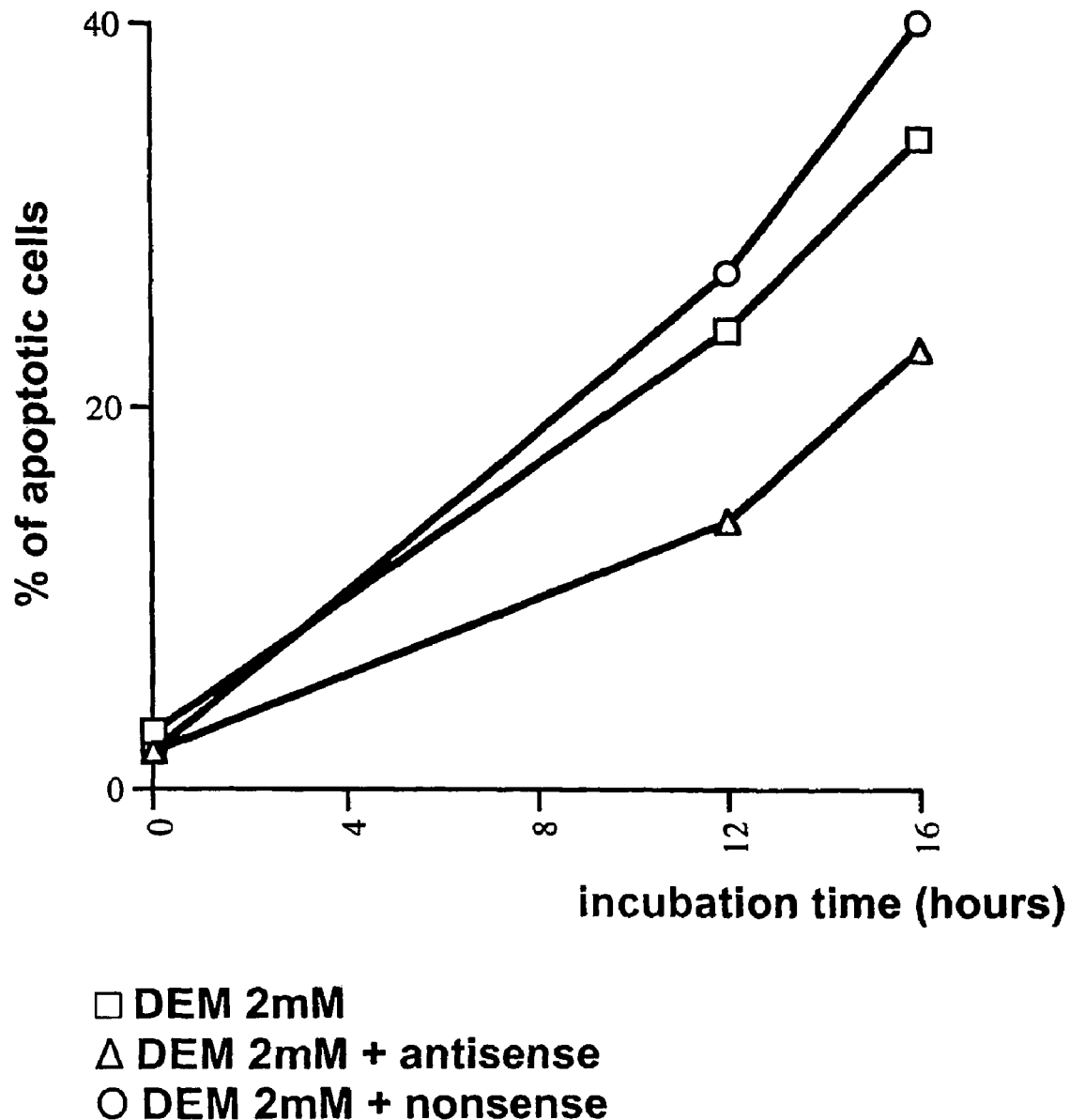
FIG. 4—Kinetics of antisense oligo effect on neuroblastoma SH-SY5Y cell apoptosis.

FIG. 4—Kinetics of the effect of antisense oligos on apoptosis in SH-SY5Y neuroblastoma cells. $3\times10^5$ cells were incubated at 37° C. in a 5% $CO_2$ atmosphere, in the presence or absence of 2 mM DEM and antisense or control oligonucleotides (7 microM). After 12 or 16 h, apoptosis was analysed as described in the text. Analogous results were obtained with any of the three antisense and the three control oligonucleotides, respectively.

Figure 5:
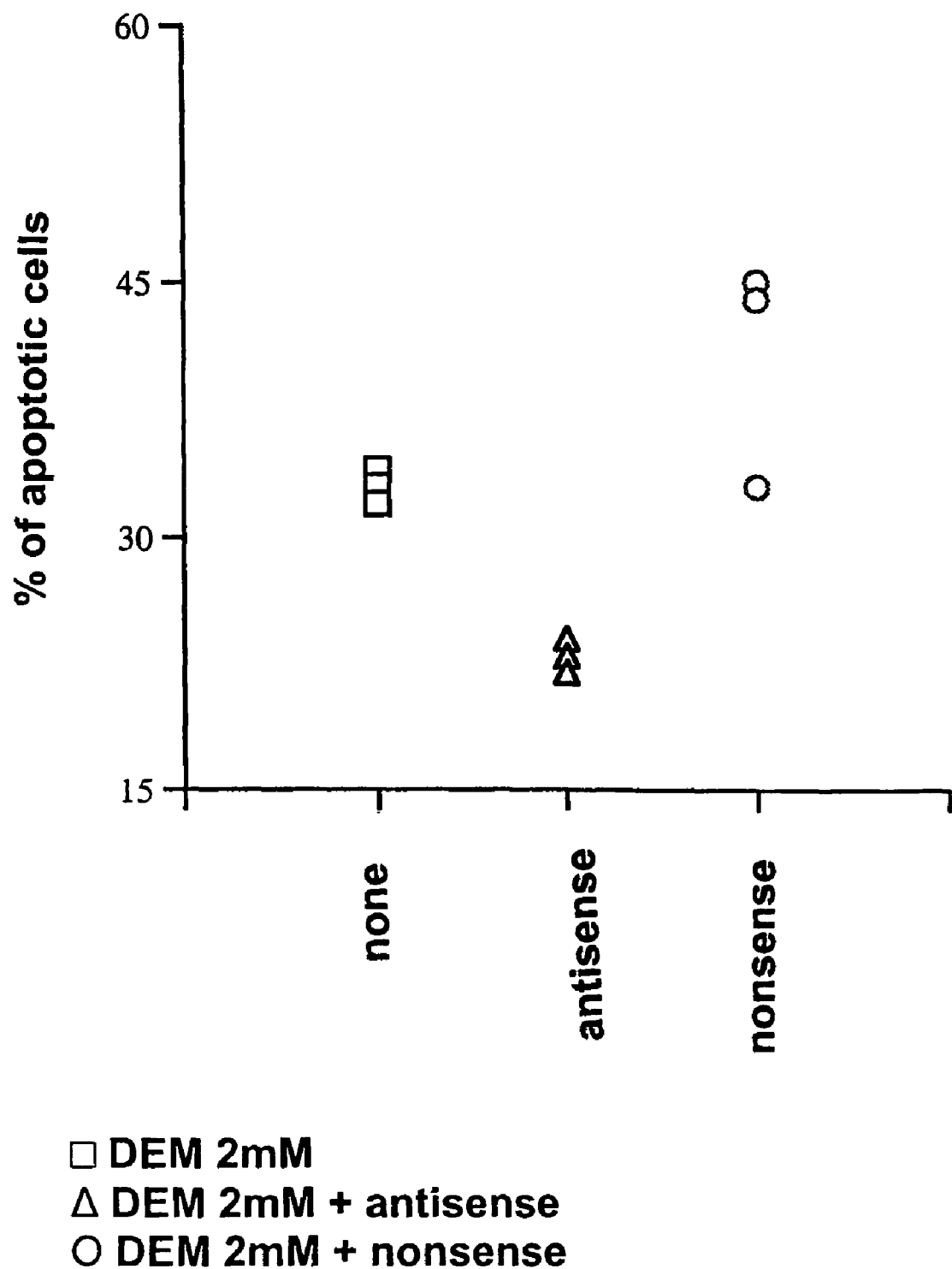
FIG. 5—Effect of antisense oligo on neuroblastoma SH-SY5Y cell apoptosis induced by 2 mM DEM.

FIG. 5—Effect of antisense oligos on apoptosis induced by 2 mM DEM in SH-SY5Y neuroblastoma cells. $3\times10^5$ cells were incubated at 37° C. in a 5% $CO_2$ atmoshere, in the absence or absence of 2 mM DEM and antisense or control oligonucleotides (7 microM). After 16 h, apoptosis was analysed as described in the text. Analogous results were obtained with any of the three antisense and the three control oligonucleotides, respectively.

Figure 6:
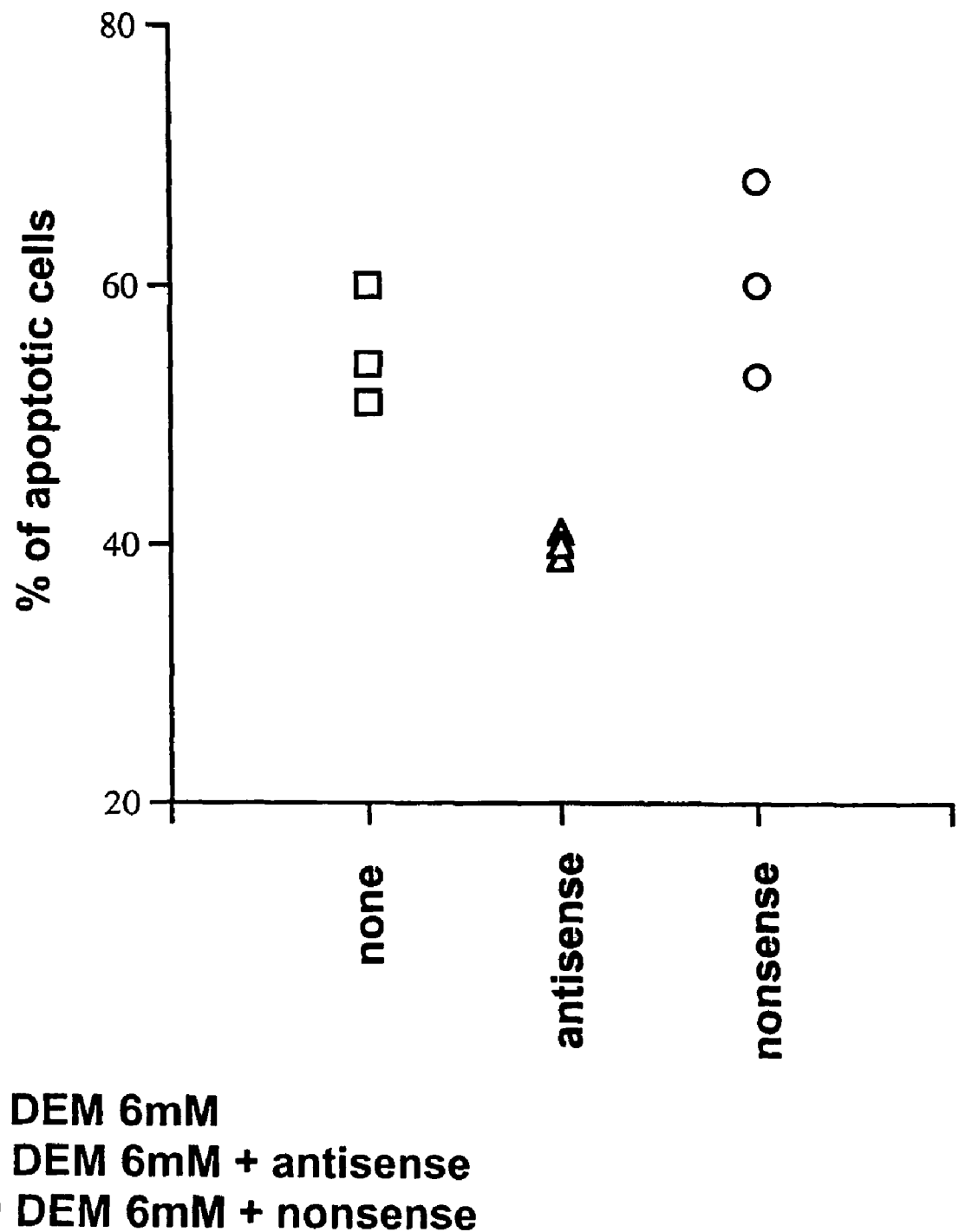
FIG. 6—Effect of antisense oligo on neuroblastoma SH-SY5Y cell apoptosis induced by 6 mM DEM.

FIG. 6—Effect of antisense oligos on apoptosis induced by 6 mM DEM in SH-SY5Y neuroblastoma cells. $3\times10^5$ cells were incubated at 37° C. in a 5% $CO_2$ atmoshere, in the absence or absence of 6 mM DEM and antisense or control oligonucleotides (7 microM). After 16 h, apoptosis was analysed as described in the text. Analogous results were obtained with any of the three antisense and the three control oligonucleotides, respectively.

FIG. 7—Intracellular expression of Air protein in cells from a patient affected by B-CLL. $2\times10^6$/ml cells obtained from patient's peripheral blood by centrifugation through Ficoll-Hypaque were incubated 24 h at 37° C. in a 5% $CO_2$ atmosphere in the absence or presence of 2 mM DEM, fixed and permeabilised with 250 microl of Cytofix/Cytoperm (Pharmingen) solution. The cells were then incubated with the specific anti-Air rabbit polyclonal or a control rabbit antibody, followed by washing with Perm/Wash (Pharmingen) and a second incubation with fluorescein isothiocyanate (FITC)-conjugated goat anti-rabbit antibody. Then the cells were analysed with a FACScan (Becton Dickinson) flow cytometer. A panel: unstimulated cells. B panel: DEM-stimulated cells. Protein expression is detected in the 33.8% of the cells in basal conditions and in the 47.6% of the cells incubated with DEM.

FIG. 8—Intracellular expression of Air protein in cells from a patient affected by B-CLL. $2\times10^6$/ml cells obtained from patient's peripheral blood by centrifugation through Ficoll-Hypaque were incubated 24 h at 37° C. in a 5% $CO_2$ atmosphere in the absence or presence of 2 mM DEM or 20 microM 2-Methoxymethylestradiol (2-ME), fixed and permeabilised with 250 microl of Cytofix/Cytoperm (Pharmingen) solution. The cells were then incubated with the specific anti-Air rabbit polyclonal or a control rabbit antibody, followed by washing with Perm/Wash (Pharmingen) and a second incubation with fluoresceinisothiocyanate (FITC)-conjugated goat anti-rabbit antibody. Then the cells were analysed with a FACScan (Becton Dickinson) flow cytometer. A panel: unstimulated cells. B panel: DEM-stimulated cells. C panel: cells stimulated with the drug 2-Methoxymethylestradiol (2-ME). Protein expression is detected in the 17.3% of the cells in basal conditions, in the 55.5% of DEM-stimulated cells and in 53.1% of 2-ME-stimulated cells.

FIG. 9—Intracellular expression of Air protein in a patient affected by B-CLL. $2\times10^6$/ml cells obtained from patient's peripheral blood by centrifugation through Ficoll-Hypaque were incubated 24 h at 37° C. in a 5% $CO_2$ atmosphere in the absence or presence of 2 mM DEM or 20 microM 2-Methoxymethylestradiol (2-ME), fixed and permeabilised with 250 microl of Cytofix/Cytoperm (Pharmingen) solution. The cells were then incubated with the specific anti-Air rabbit polyclonal or a control rabbit antibody, followed by washing with Perm/Wash (Pharmingen) and a second incubation with fluoresceinisothiocyanate (FITC)-conjugated goat anti-rabbit antibody. Then the cells were analysed with a FACScan (Becton Dickinson) flow cytometer. A panel: unstimulated cells. B panel: DEM-stimulated cells. C panel: cells stimulated with the drug 2-Methoxymethylestradiol (2-ME). Protein expression is detected in the 27.2% of the cells in basal conditions, in the 28.3% of DEM-stimulated cells and in the 23.1% of 2-ME-stimulated cells.

FIG. 10—Effect of antisense oligonucleotides on acute myeloblastic leukemia (AML) cell apoptosis induced by topotecan. $1\times10^6$/ml cells obtained from patient's peripheral blood by centrifugation through, Ficoll-Hypaque were incubated 5 days at 37° C. in a 5 $CO_2$ atmosphere in the absence or presence of antisense or control oligos (7 microM) and 50 ng/ml of topotecan. Then cell apoptosis was analyzed as described in the text. Analogous results were obtained with any of the three antisense and the three control oligonucleotides, respectively.

Figure 11A:
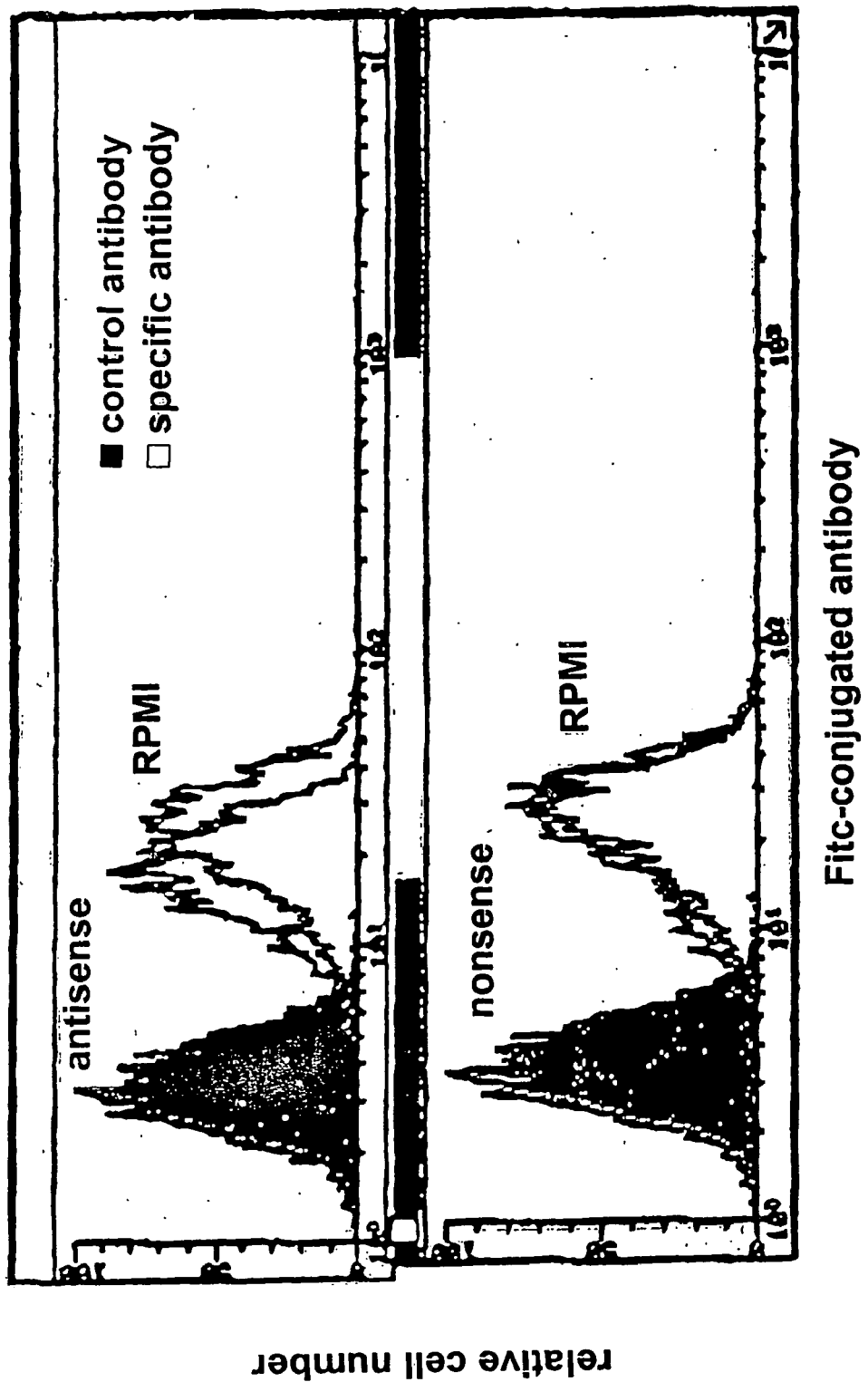
FIG. 11A—Downmodulation of Air expression (A panel) by antisense oligonucleotides.
Figure 11B:
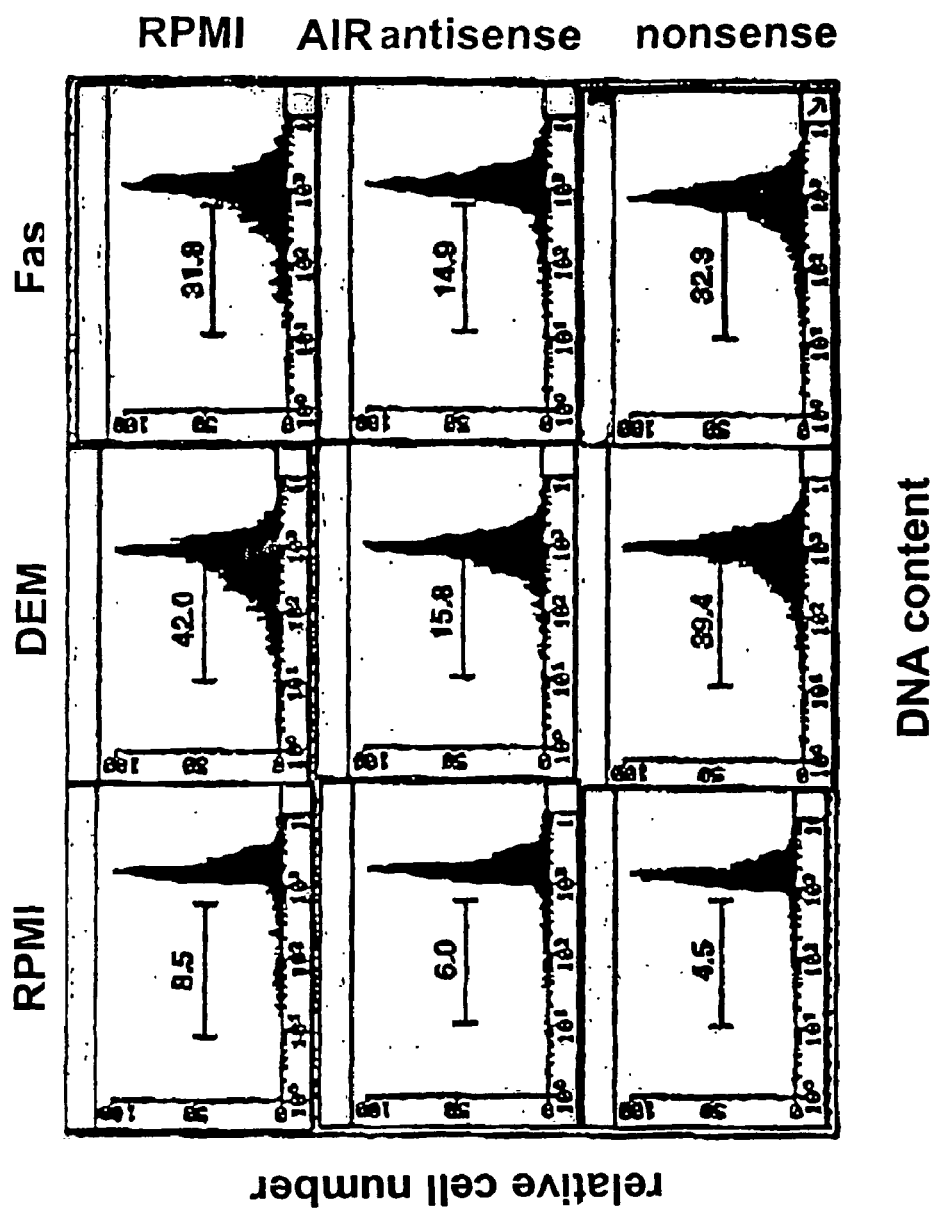
FIG. 11B—Downmodulation of Jurkat cell apoptosis (B panel) by antisense oligonucleotides.

FIG. 11—Downmodulation of Air expression and Jurkat cell apoptosis by antisense oligonucleotides. A panel. AIR antisense oligonucleotides downmodulate Air expression in Jurkat cells. Jurkat cells were incubated in the presence of the AIR antisense oligonucleotide (ODN) or a nonsense ODN. After 24 hours, the cells were fixed, permeabilized and stained with rabbit anti-Air polyclonal antibody. A second staining was performed with a FITC-anti rabbit antibodies, then the samples were analysed by flow cytometry. B Panel. AIR antisense downmodulates apoptosis in Jurkat cells. Jurkat cells were incubated with the anti-Fas antibody CH-11 (50 ng/ml) or with DEM (1 mM), in 10% FCS RPMI at 37° C. in a 5% $CO_2$ atmosphere, in the absence or the presence of AIR antisense oligonucleotide (ODN) or nonsense ODN. After 24 hours, apoptosis was analysed by PI staining and flow citometry.

Figure 12A:
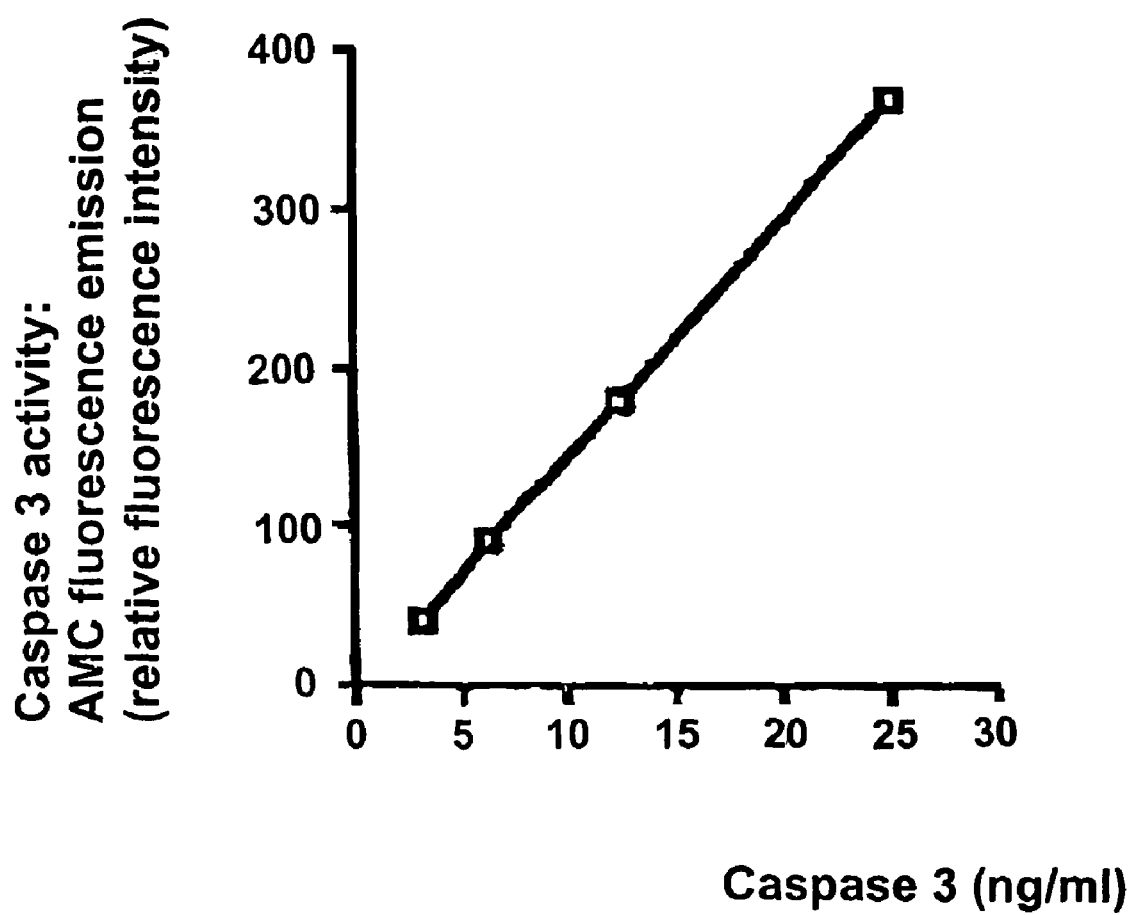
FIG. 12A—Downmodulation of caspase 3 activity in Jurkat cells by antisense oligonucleotides. (A panel) A dose/response curve of the pure enzyme is shown.
Figure 12B:
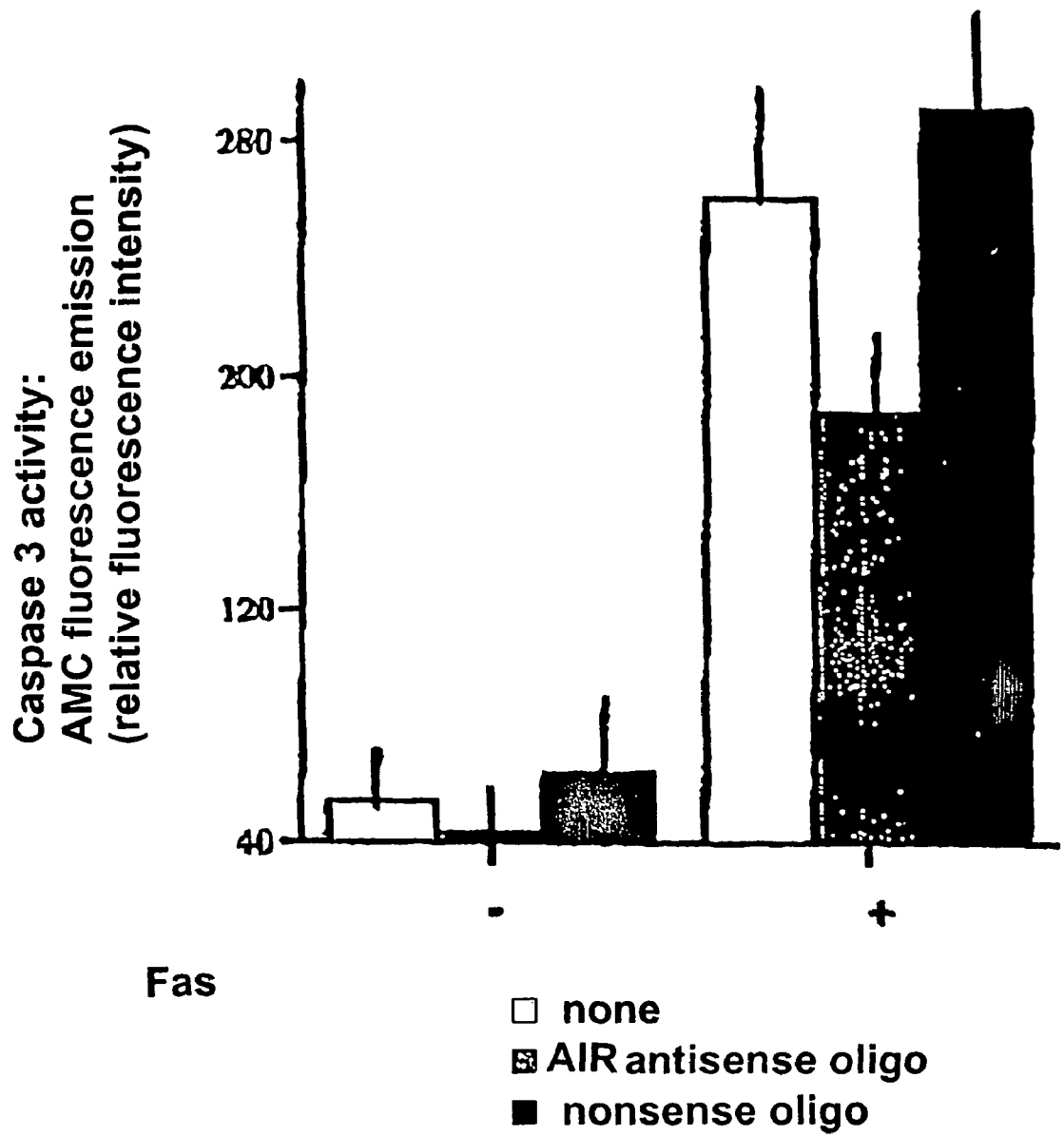
FIG. 12B—Downmodulation of caspase 3 activity in Jurkat cells by antisense oligonucleotides. (B panel) AMC fluorescence emission.

FIG. 12—Downmodulation of caspase 3 activity in Jurkat cells by antisense oligonucleotides. AIR antisense oligonucleotides downmodulate caspase 3 activity in Jurkat cells. Jurkat cells were incubated with the anti-Fas antibody CH-11 (50 ng/ml) or with DEM (1 mM), in 10% FCS RPMI at 37° C. in a 5% C02 atmosphere, in the absence or the presence of AIR antisense oligonucleotide (ODN) or nonsense ODN. After 4 hours, cell lysates were obtained and caspase 3 activity was determined by analyzing the release of 7-amino-4-methylcoumarin (AMC) from N-acetyl-DEVD-AMC by a spectrofluorimeter. A dose/response curve of the pure enzyme is shown.

Figure 13A:
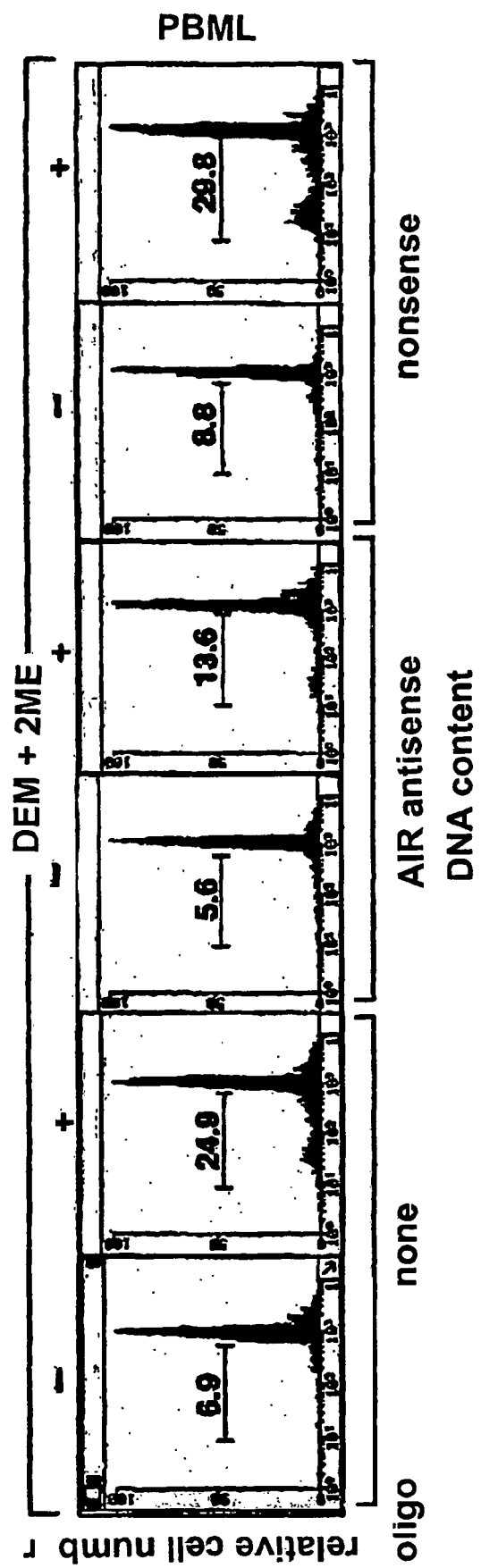
FIG. 13A—Downmodulation of apoptosis in human primary ex vivo peripheral blood mononuclear cells (PBMC) by AIR antisense oligonucleotides. (A panel): effect on PBMC.
Figure 13B:
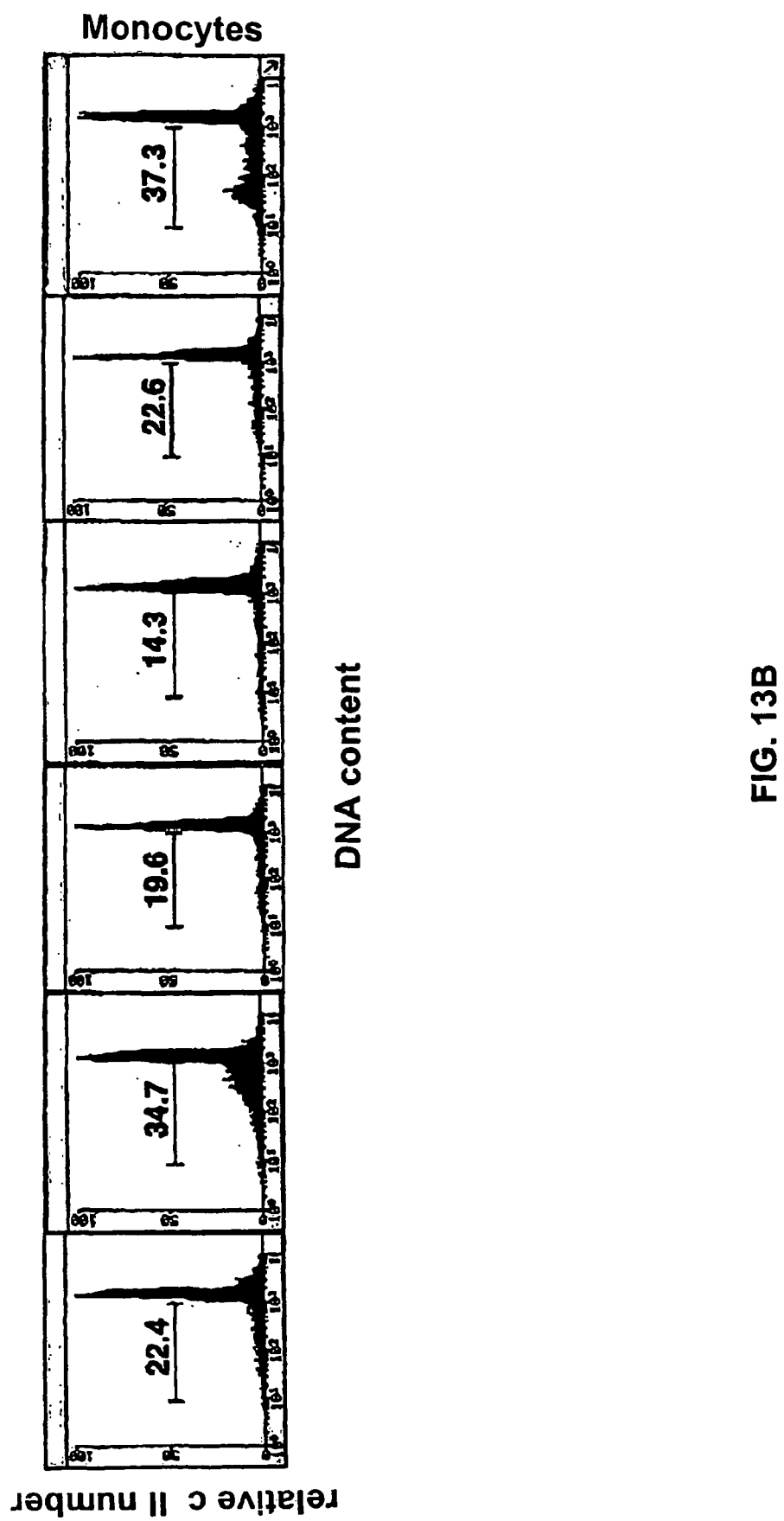
FIG. 13B—Downmodulation of apoptosis in human primary ex vivo peripheral blood mononuclear cells (PBMC) by AIR antisense oligonucleotides. (B panel): effect on monocytes.

FIG. 13—Downmodulation of apoptosis in human primary ex vivo peripheral blood mononuclear cells (PBMC) by AIR antisense oligonucleotides. Peripheral blood mononuclear cells (PBMC) were obtained from normal donors' peripheral blood by centrifugation through Ficoll-Hypaque and purified monocytes (>80% pure) were isolated by centrifugation through a 50-52% Percoll density gradient. The cells were incubated with DEM (2 mM)+2ME (20 microM), in 10% FCS RPMI at 37° C. in a 5% C02 atmosphere, in the absence or the presence of AIR antisense oligonucleotide (ODN) or nonsense ODN. Apoptosis was analysed by CD3 or CD20/annexin V-FITC double staining in immunofluorescence after 24 hours or by PI staining of permeabilised cells, as described in the text, after 3 days of incubation.

Figure 14A:
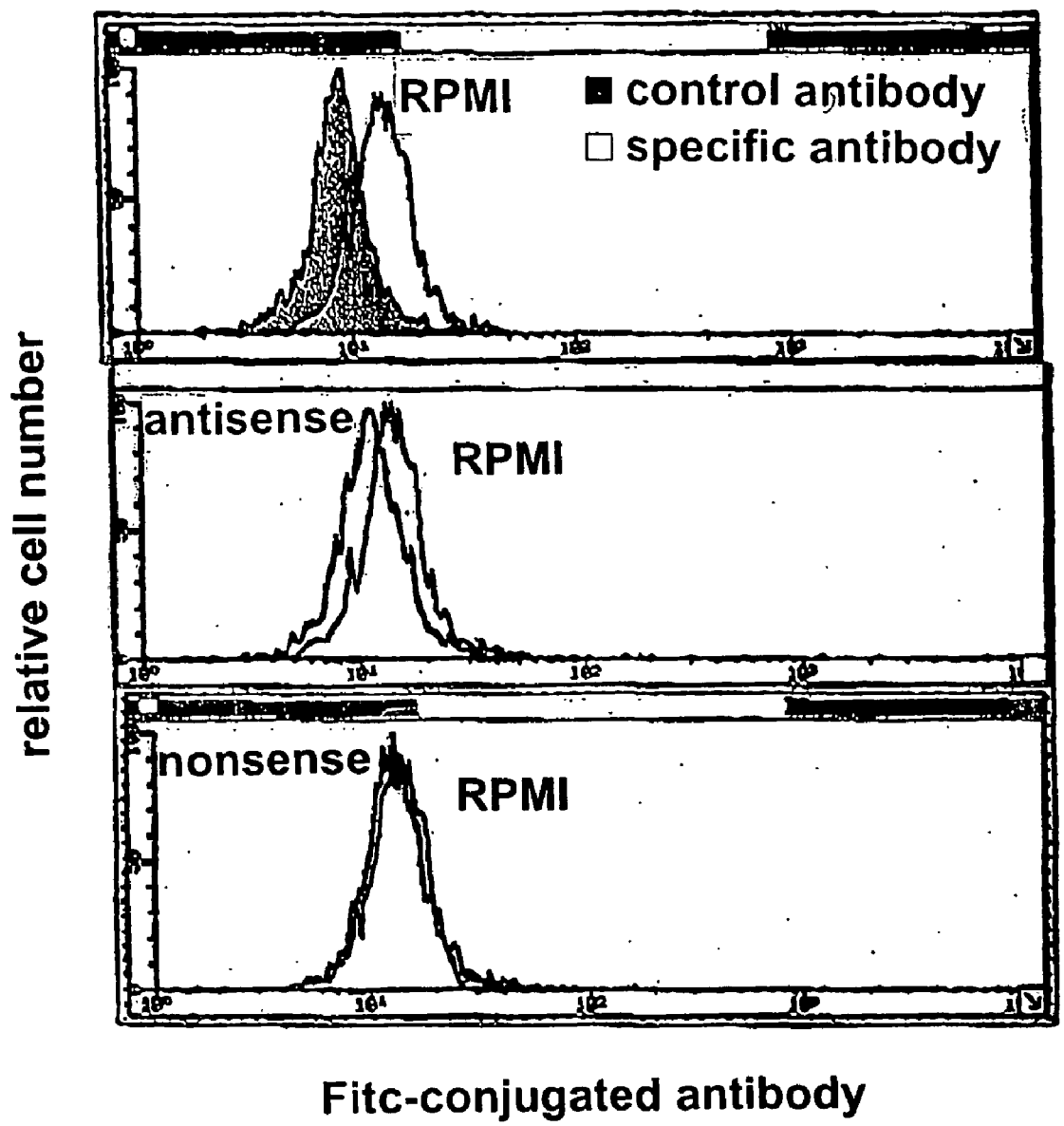
FIG. 14A—Downmodulation of Air expression (A panel) by antisense oligonucleotides.
Figure 14B:
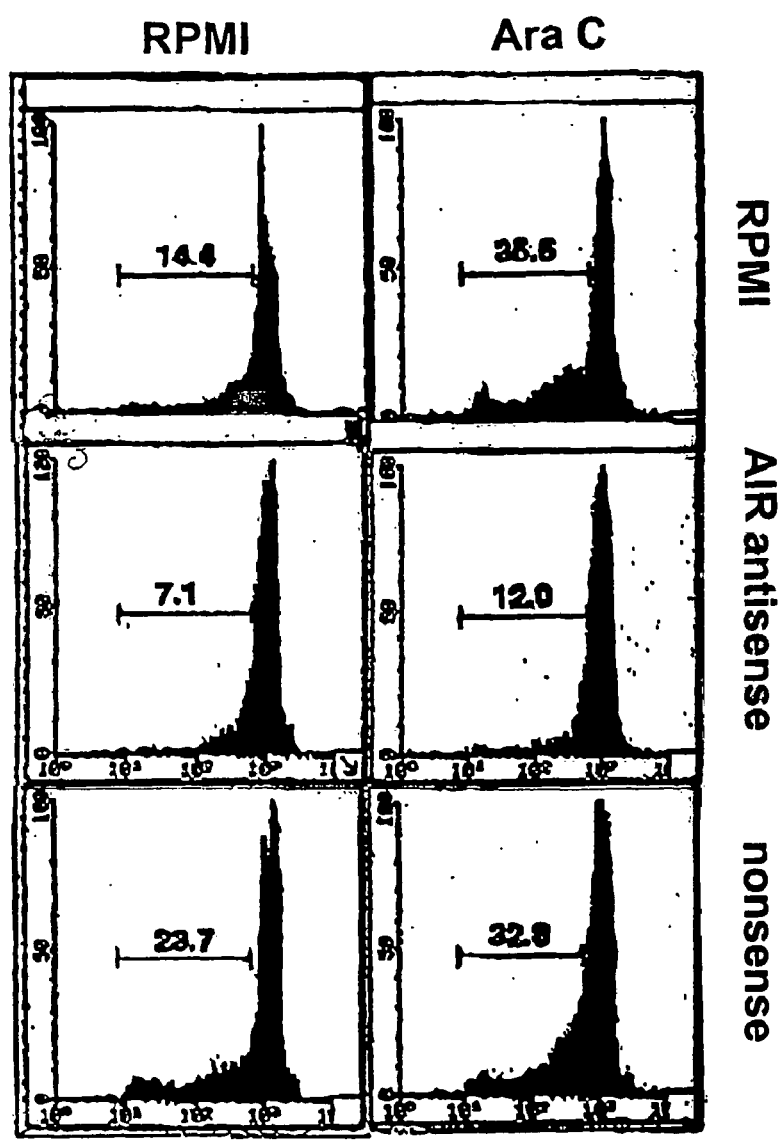
FIG. 14B—Acute myeloblastic leukemia (AML) cell apoptosis (B panel) by antisense oligonucleotides.

FIG. 14—Downmodulation of Air expression and acute myeloblastic leukemia (AML) cell apoptosis by antisense oligonucleotides. A panel. AIR antisense oligonucleotides downmodulate Air expression in acute myeloid leukaemia (AML) cells. AML cells, obtained from patient's peripheral blood by centrifugation through Ficoll-Hypaque, were incubated in the presence of the AIR antisense oligonucleotide (ODN) or a nonsense ODN. After 24 hours, the cells were fixed, permeabilized and stained with a rabbit anti-Air antibody. A second staining was performed with a FITC-anti rabbit antibodies, then the samples were analysed by flow citometry. B Panel. AIR antisense oligonucleotides downmodulate apoptosis in AML cells. AML cells, obtained from patient's peripheral blood by centrifugation through Ficoll-Hypaque, were incubated with Ara C (32 microM) in 10% FCS RPMI at 37° C. in a 50% C02 atmosphere, in the absence or the presence of AIR antisense oligonucleotide (ODN) or nonsense ODN. After 3 days the cells were collected and apoptosis was analysed by PI staining and flow citometry, as described in the text.

Figure 15A:
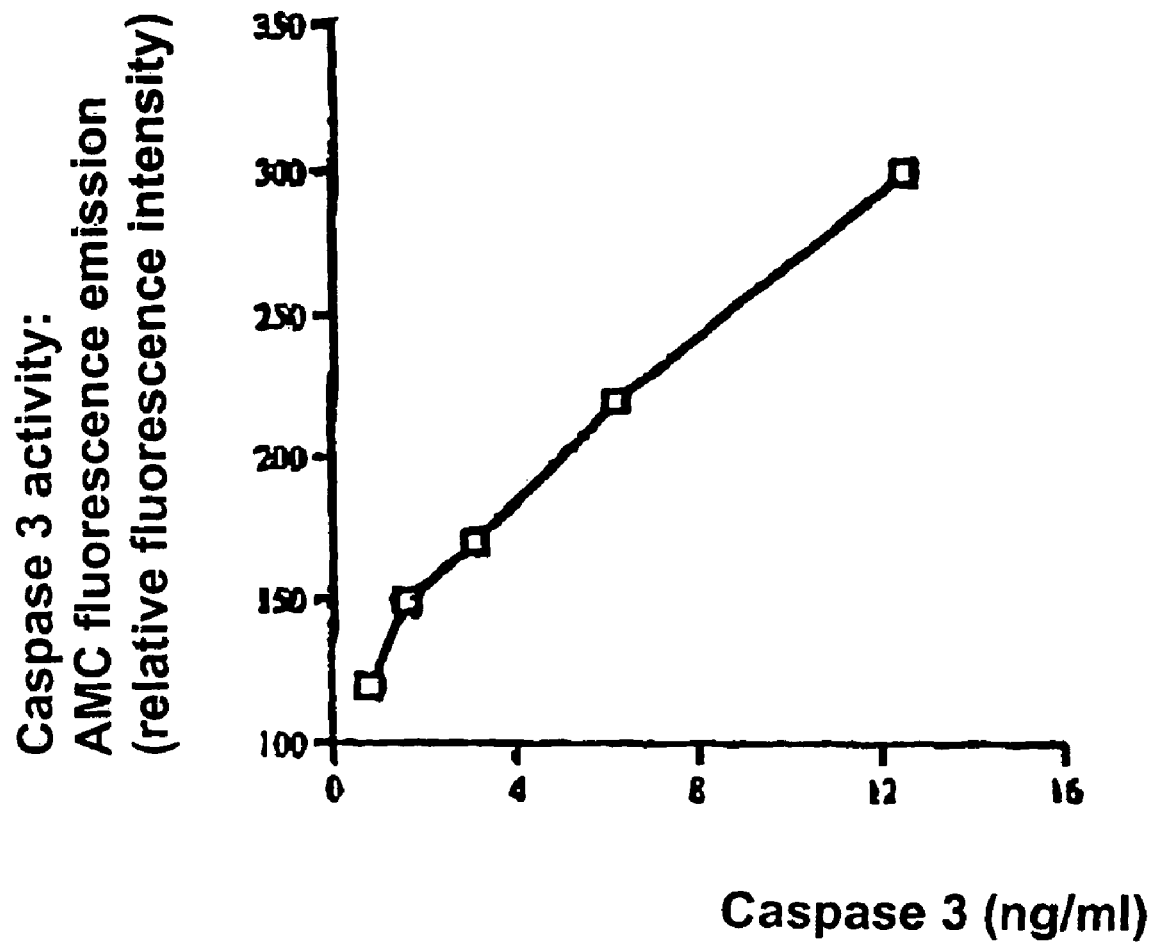
FIG. 15A—Downmodulation of caspase 3 activity in AML cells by antisense oligonucleotides. (A panel) A dose/response curve of the pure enzyme is shown.
Figure 15B:
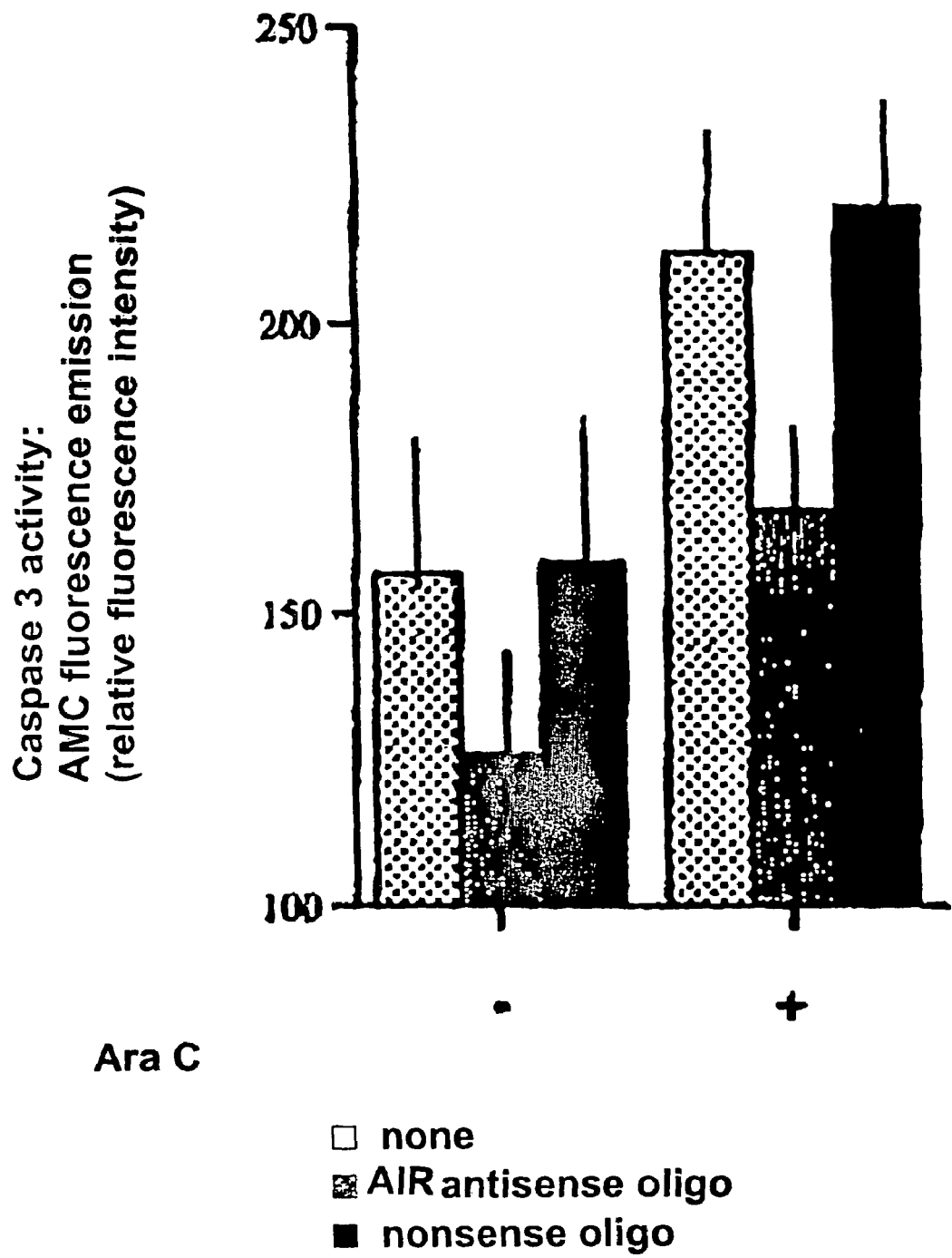
FIG. 15B—Downmodulation of caspase 3 activity in AML cells by antisense oligonucleotides. (B panel) AMC fluorescence emission.

FIG. 15—Downmodulation of caspase 3 activity in AML cells by antisense oligonucleotides. AML cells, obtained from patient's peripheral blood by centrifugation through Ficoll-Hypaque, were incubated with Ara C (32 microM) in 10% FCS RPMI at 37° C. in a 5% C02 atmosphere, in the absence or the presence of AIR antisense oligonucleotide (ODN) or nonsense. After 8 hours, cell lysates were obtained and caspase 3 activity was determined by analyzing the release of 7-amino-4-methylcoumarin (AMC) from N-acetyl-DEVD-AMC by a spectrofluorimeter. A dose/response curve of the pure enzyme is also shown.

Figure 16A:
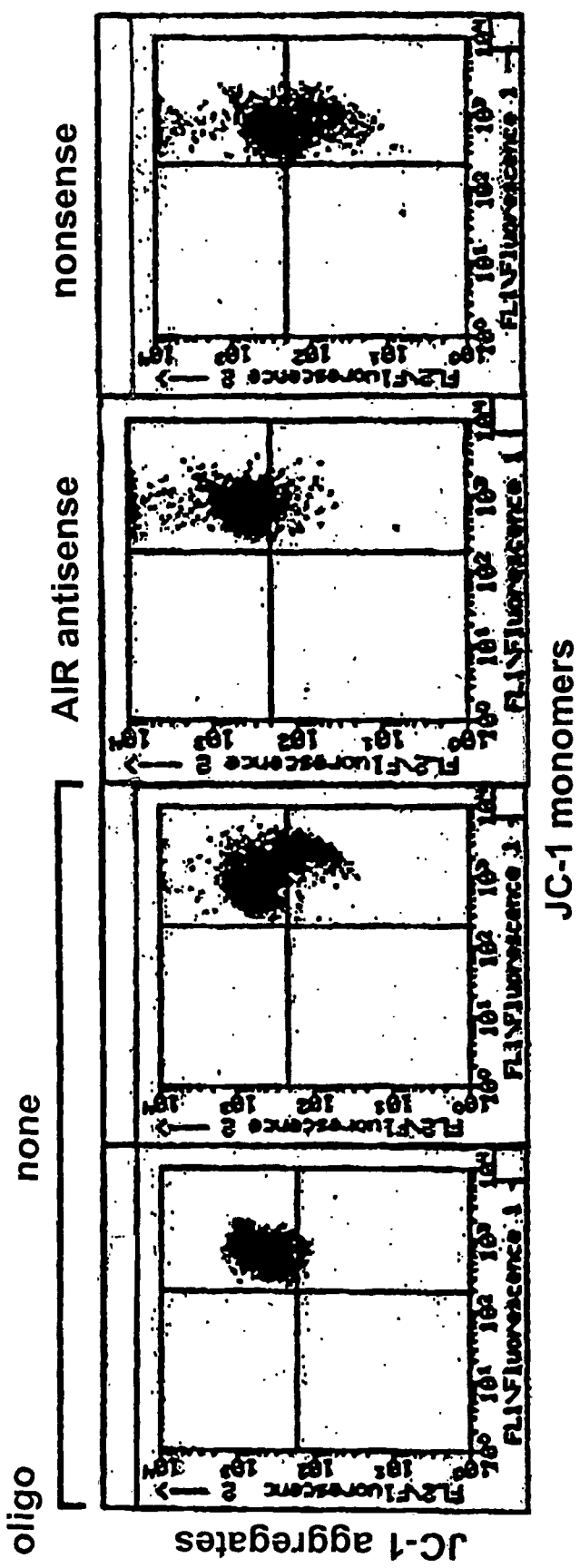
FIG. 16A—Effect of AIR antisense oligonucleotides on mitochondrion depolarization and annexin V binding in Jurkat cells. (A panel) Mitochondrion depolarization is evaluated by JC-1 staining.
Figure 16B:
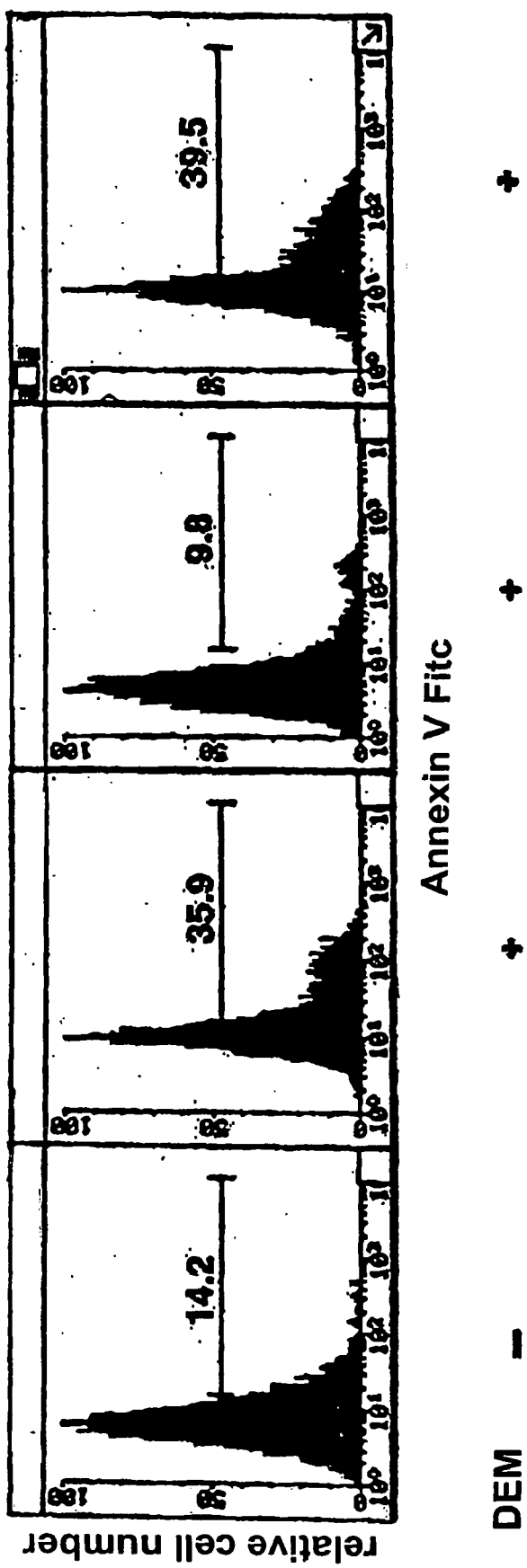
FIG. 16B—Effect of AIR antisense oligonucleotides on mitochondrion depolarization and annexin V binding in Jurkat cells. (B panel) Annexin V binding is evaluated in immunofluorescence.

FIG. 16—Effect of AIR antisense oligonucleotides on mitochondrion depolarization and annexin V binding in Jurkat cells. Jurkat cells were incubated with DEM (1mM), in 10% FCS RPMI at 37° C. in a 5% C02 atmosphere, in the absence or the presence of AIR antisense oligonucleotide (ODN) or nonsense ODN. A panel: After 3 hours, mithocondria depolarisation was analysed by staining the cells with the lipophilic cation 5,5',6,6'tetrachloro-1,1',3,3'-tetraethylbenzimidazolcarbocyanine iodide (JC-1). B panel: Annexin V binding was analysed by immunofluorescence.

FIG. 17—Staining of HeLa cells with anti-Air polyclonal antibodies. HeLa cells were stimulated with DEM (1 mM), in 10% FCS RPMI at 37° C. in a 5% C02 atmosphere for 6 hours, fixed, permeabilized and incubated with a rabbit anti-Air polyclonal antibody, followed by incubation with a rhodamine conjugated anti-rabbit antibody.

REFERENCES

1. Green D R, *Cell* 102:1, 2000.
2. Nicoletti I et al, *J. Immunol Methods* 139: 271, 1991.
3. Liang P, Pardee A B, *Methods Mol. Biol.* 85: 3, 1997.
4. Sambrok J, Fritsch E F, Maniatis T: *Molecular Cloning: A Laboratory Manual.* Second E. CSH Laboratory Press, CSH, New York, N.Y., 1989.
5. Granelli-Pipemo A, Nolan P: *J. Immunol.* 147: 2734, 1991.
6. Lamberti A et al., *Apoptosis* 4: 179, 1999.
7. Tassone P et al, *Tissue Antigens* 51: 671, 1998.
8. Romano M F et al., *Blood* 92 990, 1998.
9. Romano M F et al., *Blood* 94: 4060, 1999.
10. Romano M F et al., *Gene Ther.* 7:1234, 2000.

The invention claimed is:

1. An isolated Apoptosis-Induced and Regulator (AIR) polynucleotide selected from the group consisting of:
   (a) a polynucleotide comprising full length SEQ ID NO: 1; and
   (b) a fragment of SEQ ID NO: 1 selected from the group consisting of:
      (i) a polynucleotide comprising full length SEQ ID NO:2, SEQ ID NO:3, SEQ ID NO:4, and SEQ ID NO:5, encoding full length SEQ ID NO:12, SEQ ID NO:13, SEQ ID NO:14, and SEQ ID NO:15, respectively; and
      (ii) a polynucleotide of at least 15 bases in length from SEQ ID NO: 4 or 5.

2. An isolated polynucleotide of claim 1, wherein said polynucleotide is selected from the group consisting of:
(a) a polynucleotide consisting of full length SEQ ID NO:1; and
(b) a fragment of SEQ ID NO:1 selected from the group consisting of a polynucleotide consisting of full length SEQ ID NO:2, SEQ ID NO:3, SEQ ID NO:4, and SEQ ID NO:5, encoding SEQ ID NO:12, SEQ ID NO:13, SEQ ID NO:14, and SEQ ID NO:15, respectively.

3. An isolated polynucleotide comprising the complement of a polynucleotide according to claim 1 or claim 2, or an antisense polynucleotide selected from the group consisting of SEQ ID NOs: 6, 7, and 8.

4. A vector comprising any one of the isolated polynucleotides of claim 1, 2, or 3.

5. The vector according to claim 4, wherein said vector is an expression vector.

6. An isolated host cell genetically engineered to contain the polynucleotide of claim 1, 2, or 3.

7. An isolated host cell genetically engineered to contain the polynucleotide of claim 1, 2, or 3 in operative association with a regulatory sequence that controls expression of the polynucleotide in the host cell.

8. A pharmaceutical composition comprising an effective amount of the polynucleotide of claim 1, 2, or 3 and a carrier for modulating cell survival and/or death.

9. A method of producing a polypeptide selected from the group consisting of SEQ ID NOs: 12, 13, 14, and 15, comprising the steps of:
a) culturing, for a period of time sufficient to express a polypeptide within a cell, a host cell genetically engineered with a polynucleotide comprising
a fragment of SEQ ID NO:1 selected from the group consisting of a polynucleotide comprising full length SEQ ID NO:2, SEQ ID NO:3, SEQ ID NO:4, and SEQ ID NO:5, which encodes SEQ ID NO:12, SEQ ID NO:13, SEQ ID NO:14, and SEQ ID NO:15, respectively; and
b) isolating the polypeptide generated from the cell of step (a).

10. A kit comprising any one of the polynucleotides of claim 1, 2, or 3 for modulating apoptosis in an isolated cell in vitro or for detecting the presence of SEQ ID NO:1 or fragments thereof in a test sample, together with instructions for modulating apoptosis.

11. A composition comprising an effective amount of the polynucleotide of claim 1, 2, or 3 to modulate survival and/or death of isolated cells in vitro.

12. A composition comprising a polynucleotide of claim 1, 2, or 3 and a carrier or diluent.

* * * * *

UNITED STATES PATENT AND TRADEMARK OFFICE
CERTIFICATE OF CORRECTION

PATENT NO.       : 7,589,185 B2
APPLICATION NO. : 10/250987
DATED            : September 15, 2009
INVENTOR(S)      : Bisogni et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 465 days.

Signed and Sealed this

Twenty-first Day of September, 2010

David J. Kappos
*Director of the United States Patent and Trademark Office*

SEQUENCE LISTING

<160> NUMBER OF SEQ ID NOS: 21

<210> SEQ ID NO 1
<211> LENGTH: 3422
<212> TYPE: DNA
<213> ORGANISM: Homo sapiens

<400> SEQUENCE: 1

```
gagtagaaga atcaagcaca attaaagatg ctaaatttat tagacctata aaatatttga      60
acgcacaaga aaaagatgaa tattatttta acggttctaa atatagcgaa atagaaatag     120
acaaattgaa aaaagatata ataaattatt ataaacataa caatttaagt cttcttattt     180
ctcaaaatgt tatcgctttt aatacttgaa cgaaaaacac cgaagacatt gaaaatatta     240
tcaatgaatc agtaggtaaa gaaaaaaaat taactagctc ggaattgtct aaaataacaa     300
aaaataaagc ttgaattgat gttgatgaaa tagtaaatca ttgagcgcaa aaagaatttg     360 atttttaataa tgatgaggat tgggttggca aattgtatta tgtaaataaa ggagattcaa     420
tatgaatacc ttctaaaaca gatactgatt ttactaaatc ccttcttaaa ttaattgata     480
aatttaaaaa taattattat tcaagtattc caattttgaa aaaagataat aattatgttt     540
cttatcctat cgatcaatta gaaaaagata ataaagaaat atataataaa acatttctag     600
ataaaatcat taattctgaa aatgctgact tattgtttag cgacaaggaa atcaatgaat     660
taacaaaatt taacatttta ttttatgcag aagaatttaa agtaaaaaac aatttaactt     720
tttgaaaaga aaatgaagat ttaataaata aattctatac gagtttttaat gttaaatcca     780
```

```
aaaaagtgtc ataccttagt tatttaatga agaaaaaata cgatgatatg aaaaaaatag    840
agaaaaaata tttatataag tttgtaaata atggtagaga atattatttt ttgaataaag    900
acaaagcaag acaatacata ataaatagtt ttttacaaat aaaaagcaat aaatatttat    960
taaaatcgaa aacttactac tactatgaca ataaggaatt tcaaagcatt ttagaattga   1020
ataaatatat aattaaaaaa agaggggaaa aataaaatga agatagaaag aaaattattt   1080
ttaaatacaa cgattttttgg atcttctatt atcatttgct ccacatcttg tgccaataat   1140
gaaacacaag aagtaaaaga taatttaaaa aatataaata cacgtggtaa aaatcaaaca   1200 tttttttacgt tagatataga taataaaaaa tatagattta aaaatgttga tgatttcgta   1260
aatagttttg attacaataa aaaaatcgaa aaatttatag cagttggaga tgatttaata   1320
aatgatgaaa aaaatatctt ttaaataatg aaaactatag ttttatcgaa aatgaaaaag   1380
attttaaaaa aatgtataag actaagtata acgaggatgt ggcgaactca gaagatgcat   1440
ataattcata tcttgaagat tatgctttga ttttaaaata ttttgcttca aataagggat   1500
tcgacagtag tgaagatgca aaacaatata atcttgataa aataaaaaaa ggcacaacat   1560
tattttcata ttataaaaac gaagagaagt tatttaatcc aatgagtttg aattctcaaa   1620
ataattttag aaaccagtac attaataatc taaaagaaat aaagtcattt gataatttca   1680 aatatttta cttttttaaat aataaagatg ttttaaaaaa cgaaaatact ataaaatttt   1740
acgaaaaata tagattagac aaaatagcag aaacaattta tgcaaacata ttaaatacaa   1800 tttttttacga aacagcaatt aatttaaaag aagaattcga aggtaaaaat tacctatatc   1860
ctgatgcaaa agatgatata ggctatcaat ttatactcaa tcctgaattt aaattaaaag   1920
gttgagacta aagggaacg aaatcaataa tatacaaaaa atgaaaagct agagaatgaa   1980
acaatttcat agaaaataaa aacgaaaata atgaaaaaga gcttttttaga agttctgtag   2040 acaatttttga gcctaatgat gaggttgtta acattttttg aacatttaac gtacactttt   2100
taggaacaaa aattaaggaa ttattggatt taaagagattt ggaaataaaa acaaataaat   2160 ttgttatga caaatattac gattgatggc aatgattggt aagaaattat gaaacaagat   2220
ctgctttttt tattggaagt aaatttctta atgagtctga tgggttagga ataaatacaa   2280
aaattgttag atttttctgaa ataaaatatg agaacatttt ggacggacaa gaatttgaaa   2340
ttaaaaaaaa tatagaacca catttaagta aattggttga aaaaataaaa caaatagtta   2400
atcaaaatga actagatttg tttagcatta atgacaattt ttatgaaaa atcaatggca   2460 aagaaaaaat ttcaaaaaaa gatactaatc tcatttcagg tttgactaaa aattataaaa   2520
aattgctaag tataataaaa aatgaaataa ttgttttttct aaataatgta attgatgaaa   2580
cttttgaatt ttatccgaaa gttaacatta acaatataaa aatgctagta aaagaaaaaa   2640
acacaaaaaa tcattttta ttttttaaata aagaaacgt ctcatttat gatttaaaaa   2700 ataatgtcaa agaaaatatt ttaataaaga aaattataaa aaagatgaa aaaataactg   2760 aaaataattt cggagaatta gtaaataaag aggaagaaag aaatttttta acatttgttt   2820 atttttatttt aaaagaaaca aaatccatta ataaagagtt agatttatgc gagccatttt   2880
gaattgaaaa cgacaaatat aaattgtata aaaaatattg tttgttagaa gatttaagaa   2940
ctttttgaaa aaaagaaaca attaactttt ttaatcatgc ctcaaaagaa gaattttcaa   3000
aaataataac agatttttat aataacaaat ttgttcctc aaaaaaatat aaatttgtta   3060
ttccaaatag aaaccacgaa atatttttta attcgaaaga acttttgtta gcaaatttat   3120
```

-continued

| ataactacct taaaataaaa aattcaacta attatattat aaataataaa agttctaaaa | 3180 |
| aaacttacaa tttaaatttt tttaatgttt atagatttaa aattaatgaa aaaatttatg | 3240 |
| atttttaaaaa ttttaatgat atagtgacat ttttttaaata ttttgtgttg caaaatgcaa | 3300 |
| aaattgataa ttaaggagga aaagtaatga aaaaatcaaa aatgaaaaaa attttttacat | 3360 |
| ctattatagg aattttacct ttaactacta ttttggtttc ttgcaaaaaa aaaaaaaaaa | 3420 |
| aa | 3422 |

<210> SEQ ID NO 2
<211> LENGTH: 1119
<212> TYPE: DNA
<213> ORGANISM: Homo Sapiens

<400> SEQUENCE: 2

| atgaagaaaa aatacgatga tatgaaaaaa atagagaaaa aatatttata taagtttgta | 60 |
| aataatggta gagaatatta tttttttgaat aaagacaaag caagacaata cataataaat | 120 |
| agttttttac aaataaaaag caataaatat ttattaaaat cgaaaactta ctactactat | 180 |
| gacaataagg aatttcaaag catttttagaa ttgaataaat atataattaa aaaaagaggg | 240 |
| gaaaataaaa tgaagataga aagaaaatta ttttttaaata caacgatttt tggatcttct | 300 |
| attatcattt gctccacatc ttgtgccaat aatgaaacac aagaagtaaa agataattta | 360 |
| aaaaatataa atacacgtgg taaaaatcaa acattttttta cgttagatat agataataaa | 420 |
| aaatatagat ttaaaaatgt tgatgatttc gtaaatagtt ttgattacaa taaaaaaatc | 480 |
| gaaaaattta tagcagttgg agatgattta ataaatgatg aaaaaaatat cttttcaaat | 540 |
| aatgaaaact atagttttat cgaaaatgaa aaagatttta aaaaaatgta taagactaag | 600 |
| tataacgagg atgtggcgaa ctcagaagat gcatataatt catatcttga agattatgct | 660 |
| ttgattttaa aatattttgc ttcaaataag ggattcgaca gtagtgaaga tgcaaaacaa | 720 |
| tataatcttg ataaaataaa aaaaggcaca acattatttt catattataa aaacgaagag | 780 |
| aagttattta atccaatgag tttgaattct caaaataatt ttagaaaacca gtacattaat | 840 |
| aatctaaaag aaataaagtc atttgataat ttcaaatatt tttacttttt aaataataaa | 900 |
| gatgttttaa aaacgaaaaa tactataaaa ttttacgaaa aatatagatt agacaaaata | 960 |
| gcagaaacaa tttatgcaaa catattaaat acaattttttt acgaaacagc aattaattta | 1020 |
| aaagaagaat tcgaaggtaa aaattaccta tatcctgatg caaaagatga tataggctat | 1080 |
| caatttatac tcaatcctga atttaaatta aaaggttga | 1119 |

<210> SEQ ID NO 3
<211> LENGTH: 534
<212> TYPE: DNA
<213> ORGANISM: Homo Sapiens

<400> SEQUENCE: 3

| atgtataaga ctaagtataa cgaggatgtg gcgaactcag aagatgcata taattcatat | 60 |
| cttgaagatt atgctttgat tttaaaatat tttgcttcaa ataagggatt cgacagtagt | 120 |
| gaagatgcaa acaatataa tcttgataaa ataaaaaaag gcacaacatt attttcatat | 180 |
| tataaaaacg aagagaagtt atttaatcca atgagtttga attctcaaaa taattttaga | 240 |
| aaccagtaca ttaataatct aaaagaaata aagtcatttg ataatttcaa atattttttac | 300 |
| ttttttaaata taaagatgt tttaaaaaac gaaaatacta taaaatttta cgaaaaatat | 360 |
| agattagaca aaatagcaga aacaatttat gcaaacatat taaatacaat ttttttacgaa | 420 |

```
acagcaatta atttaaaaga agaattcgaa ggtaaaaatt acctatatcc tgatgcaaaa      480
gatgatatag gctatcaatt tatactcaat cctgaattta aattaaaagg ttga            534

<210> SEQ ID NO 4
<211> LENGTH: 288
<212> TYPE: DNA
<213> ORGANISM: Homo Sapiens

<400> SEQUENCE: 4
atgaagatag aaagaaaatt attttttaaat acaacgattt ttggatcttc tattatcatt      60
tgctccacat cttgtgccaa taatgaaaca caagaagtaa aagataattt aaaaaatata    120
aatacacgtg gtaaaaatca aacatttttt acgttagata tagataataa aaatataga     180 tttaaaaatg ttgatgattt cgtaaatagt tttgattaca ataaaaaaat cgaaaaattt    240
atagcagttg gagatgattt aataaatgat gaaaaaaata tcttttaa                  288

<210> SEQ ID NO 5
<211> LENGTH: 249
<212> TYPE: DNA
<213> ORGANISM: Homo Sapiens

<400> SEQUENCE: 5
atgaagaaaa aatacgatga tatgaaaaaa atagagaaaa aatatttata taagtttgta      60
aataatggta gagaatatta ttttttgaat aaagacaaag caagacaata cataataaat    120
agttttttac aaataaaaag caataaatat ttattaaaat cgaaaactta ctactactat    180
gacaataagg aatttcaaag cattttagaa ttgaataaat atataattaa aaaagagggg    240
gaaaaataa                                                             249

<210> SEQ ID NO 6
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 6
cttagtctta tacatttttt taaaatc                                          27

<210> SEQ ID NO 7
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 7
atcttagtct tatacatttt tttaaa                                           26

<210> SEQ ID NO 8
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 8
ctttctatct tcattttatt tttcc                                            25

<210> SEQ ID NO 9
```

-continued

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
tttttcttca ttaaataact aagg                                              24

<210> SEQ ID NO 10
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 10
caattcttga ttattattct taaattc                                           27

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 11
ttatattcta ttatatttat gaactcc                                           27

<210> SEQ ID NO 12
<211> LENGTH: 372
<212> TYPE: PRT
<213> ORGANISM: Homo Sapiens
<220> FEATURE:
<221> NAME/KEY: MISC_FEATURE
<222> LOCATION: (1)..(372)
<223> OTHER INFORMATION: Protein encoded by SEQ.ID.NO.2

<400> SEQUENCE: 12

Met Lys Lys Tyr Asp Asp Met Lys Lys Ile Glu Lys Lys Tyr Leu
1               5                   10                  15

Tyr Lys Phe Val Asn Asn Gly Arg Glu Tyr Tyr Phe Leu Asn Lys Asp
            20                  25                  30

Lys Ala Arg Gln Tyr Ile Ile Asn Ser Phe Leu Gln Ile Lys Ser Asn
        35                  40                  45

Lys Tyr Leu Leu Lys Ser Lys Thr Tyr Tyr Tyr Asp Asn Lys Glu
    50                  55                  60

Phe Gln Ser Ile Leu Glu Leu Asn Lys Tyr Ile Ile Lys Lys Arg Gly
65                  70                  75                  80

Glu Asn Lys Met Lys Ile Glu Arg Lys Leu Phe Leu Asn Thr Thr Ile
                85                  90                  95

Phe Gly Ser Ser Ile Ile Ile Cys Ser Thr Ser Cys Ala Asn Asn Glu
            100                 105                 110

Thr Gln Glu Val Lys Asp Asn Leu Lys Asn Ile Asn Thr Arg Gly Lys
        115                 120                 125

Asn Gln Thr Phe Phe Thr Leu Asp Ile Asp Asn Lys Lys Tyr Arg Phe
    130                 135                 140

Lys Asn Val Asp Asp Phe Val Asn Ser Phe Asp Tyr Asn Lys Lys Ile
145                 150                 155                 160

Glu Lys Phe Ile Ala Val Gly Asp Asp Leu Ile Asn Asp Glu Lys Asn
                165                 170                 175
```

```
Ile Phe Ser Asn Asn Glu Asn Tyr Ser Phe Ile Glu Asn Glu Lys Asp
                180                 185                 190

Phe Lys Lys Met Tyr Lys Thr Lys Tyr Asn Glu Asp Val Ala Asn Ser
            195                 200                 205

Glu Asp Ala Tyr Asn Ser Tyr Leu Glu Asp Tyr Ala Leu Ile Leu Lys
            210                 215                 220

Tyr Phe Ala Ser Asn Lys Gly Phe Asp Ser Ser Glu Asp Ala Lys Gln
225                 230                 235                 240

Tyr Asn Leu Asp Lys Ile Lys Lys Gly Thr Thr Leu Phe Ser Tyr Tyr
                245                 250                 255

Lys Asn Glu Glu Lys Leu Phe Asn Pro Met Ser Leu Asn Ser Gln Asn
            260                 265                 270

Asn Phe Arg Asn Gln Tyr Ile Asn Asn Leu Lys Glu Ile Lys Ser Phe
            275                 280                 285

Asp Asn Phe Lys Tyr Phe Tyr Phe Leu Asn Asn Lys Asp Val Leu Lys
            290                 295                 300

Asn Glu Asn Thr Ile Lys Phe Tyr Glu Lys Tyr Arg Leu Asp Lys Ile
305                 310                 315                 320

Ala Glu Thr Ile Tyr Ala Asn Ile Leu Asn Thr Ile Phe Tyr Glu Thr
                325                 330                 335

Ala Ile Asn Leu Lys Glu Glu Phe Glu Gly Lys Asn Tyr Leu Tyr Pro
            340                 345                 350

Asp Ala Lys Asp Asp Ile Gly Tyr Gln Phe Ile Leu Asn Pro Glu Phe
            355                 360                 365

Lys Leu Lys Gly
    370

<210> SEQ ID NO 13
<211> LENGTH: 177
<212> TYPE: PRT
<213> ORGANISM: Homo Sapiens
<220> FEATURE:
<221> NAME/KEY: MISC_FEATURE
<222> LOCATION: (1)..(177)
<223> OTHER INFORMATION: Protein encoded by SEQ.ID NO.3

<400> SEQUENCE: 13

Met Tyr Lys Thr Lys Tyr Asn Glu Asp Val Ala Asn Ser Glu Asp Ala
1               5                   10                  15

Tyr Asn Ser Tyr Leu Glu Asp Tyr Ala Leu Ile Leu Lys Tyr Phe Ala
                20                  25                  30

Ser Asn Lys Gly Phe Asp Ser Ser Glu Asp Ala Lys Gln Tyr Asn Leu
            35                  40                  45

Asp Lys Ile Lys Lys Gly Thr Thr Leu Phe Ser Tyr Tyr Lys Asn Glu
        50                  55                  60

Glu Lys Leu Phe Asn Pro Met Ser Leu Asn Ser Gln Asn Asn Phe Arg
65                  70                  75                  80

Asn Gln Tyr Ile Asn Asn Leu Lys Glu Ile Lys Ser Phe Asp Asn Phe
                85                  90                  95

Lys Tyr Phe Tyr Phe Leu Asn Asn Lys Asp Val Leu Lys Asn Glu Asn
            100                 105                 110

Thr Ile Lys Phe Tyr Glu Lys Tyr Arg Leu Asp Lys Ile Ala Glu Thr
        115                 120                 125

Ile Tyr Ala Asn Ile Leu Asn Thr Ile Phe Tyr Glu Thr Ala Ile Asn
    130                 135                 140

Leu Lys Glu Glu Phe Glu Gly Lys Asn Tyr Leu Tyr Pro Asp Ala Lys
```

```
                145                 150                 155                 160
Asp Asp Ile Gly Tyr Gln Phe Ile Leu Asn Pro Glu Phe Lys Leu Lys
                    165                 170                 175

Gly

<210> SEQ ID NO 14
<211> LENGTH: 95
<212> TYPE: PRT
<213> ORGANISM: Homo Sapiens
<220> FEATURE:
<221> NAME/KEY: MISC_FEATURE
<222> LOCATION: (1)..(95)
<223> OTHER INFORMATION: Protein encoded by SE.ID.NO.4

<400> SEQUENCE: 14

Met Lys Ile Glu Arg Lys Leu Phe Leu Asn Thr Thr Ile Phe Gly Ser
1               5                   10                  15

Ser Ile Ile Ile Cys Ser Thr Ser Cys Ala Asn Asn Glu Thr Gln Glu
                20                  25                  30

Val Lys Asp Asn Leu Lys Asn Ile Asn Thr Arg Gly Lys Asn Gln Thr
            35                  40                  45

Phe Phe Thr Leu Asp Ile Asp Asn Lys Lys Tyr Arg Phe Lys Asn Val
    50                  55                  60

Asp Asp Phe Val Asn Ser Phe Asp Tyr Asn Lys Lys Ile Glu Lys Phe
65                  70                  75                  80

Ile Ala Val Gly Asp Asp Leu Ile Asn Asp Glu Lys Asn Ile Phe
                85                  90                  95

<210> SEQ ID NO 15
<211> LENGTH: 82
<212> TYPE: PRT
<213> ORGANISM: Homo Sapiens
<220> FEATURE:
<221> NAME/KEY: MISC_FEATURE
<222> LOCATION: (1)..(82)
<223> OTHER INFORMATION: Protein encoded by SEQ.ID.NO.5

<400> SEQUENCE: 15

Met Lys Lys Lys Tyr Asp Asp Met Lys Lys Ile Glu Lys Lys Tyr Leu
1               5                   10                  15

Tyr Lys Phe Val Asn Asn Gly Arg Glu Tyr Tyr Phe Leu Asn Lys Asp
                20                  25                  30

Lys Ala Arg Gln Tyr Ile Ile Asn Ser Phe Leu Gln Ile Lys Ser Asn
            35                  40                  45

Lys Tyr Leu Leu Lys Ser Lys Thr Tyr Tyr Tyr Asp Asn Lys Glu
    50                  55                  60

Phe Gln Ser Ile Leu Glu Leu Asn Lys Tyr Ile Ile Lys Lys Arg Gly
65                  70                  75                  80

Glu Lys

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide

<400> SEQUENCE: 16

Asn Ser Gln Asn Asn Phe Arg Asn Gln Tyr Ile Asn Asn Leu Lys Glu
1               5                   10                  15
```

```
Ile Lys Ser

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide

<400> SEQUENCE: 17

Lys Phe Tyr Glu Lys Tyr Arg Leu Asp Lys Ile Ala Glu Thr Ile Tyr
1               5                   10                  15

Ala

<210> SEQ ID NO 18
<211> LENGTH: 18
<212> TYPE: PRT
<213> ORGANISM: Artificial Sequence
<220> FEATURE:
<223> OTHER INFORMATION: Synthetic peptide

<400> SEQUENCE: 18

Asn Leu Lys Glu Glu Phe Glu Gly Lys Asn Tyr Leu Tyr Pro Asp Ala
1               5                   10                  15

Lys Asp

<210> SEQ ID NO 19
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 19
caacggcagg ggaatctccc tctcctt                                    27

<210> SEQ ID NO 20
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 20
caacggcagg ggaatctccc tctcctt                                    27

<210> SEQ ID NO 21
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 21
aagcttaacg agg                                                   13
```